(12) United States Patent
Nikolchev et al.

(10) Patent No.: US 7,785,361 B2
(45) Date of Patent: Aug. 31, 2010

(54) IMPLANT DELIVERY TECHNOLOGIES

(76) Inventors: Julian Nikolchev, 251 Duranzo Way, Portola Valley, CA (US) 94028; Dai T. Ton, 1514 Mt. Diablo Ave., Milpitas, CA (US) 95035; William R. George, 435 Oxford Way, Santa Cruz, CA (US) 95060; Nicholas C. Debeer, 435 Oxford Way, Santa Cruz, CA (US) 95060

( * ) Notice: Subject to any disclaimer, the term of this patent is extended or adjusted under 35 U.S.C. 154(b) by 837 days.

(21) Appl. No.: 10/550,707

(22) PCT Filed: Mar. 23, 2004

(86) PCT No.: PCT/US2004/008909
§ 371 (c)(1),
(2), (4) Date: Jun. 26, 2006

(87) PCT Pub. No.: WO2004/087006
PCT Pub. Date: Oct. 14, 2004

(65) Prior Publication Data
US 2007/0043419 A1    Feb. 22, 2007

Related U.S. Application Data

(63) Continuation of application No. 10/745,778, filed on Dec. 24, 2003.

(51) Int. Cl.
A61F 2/06 (2006.01)
(52) U.S. Cl. ..................................... 623/1.11
(58) Field of Classification Search ............... 623/1.11, 623/1.12, 1.23; 606/108, 200, 191–198
See application file for complete search history.

(56) References Cited

U.S. PATENT DOCUMENTS

| | | | |
|---|---|---|---|
| 4,503,569 | A | 3/1985 | Dotter |
| 4,512,338 | A | 4/1985 | Balko et al. |
| 4,553,545 | A | 11/1985 | Maass et al. |
| 4,562,596 | A | 1/1986 | Kornberg |
| 4,580,568 | A | 4/1986 | Gianturco |
| 4,655,771 | A | 4/1987 | Wallsten |
| 4,665,918 | A | 5/1987 | Garza et al. |
| 4,732,152 | A | 3/1988 | Wallsten et al. |

(Continued)

FOREIGN PATENT DOCUMENTS

DE    4420142    12/1995

(Continued)

OTHER PUBLICATIONS

Supplementary European Search Report of EP Application No. 04758233, mailed Nov. 7, 2007, 7 pages total.

(Continued)

*Primary Examiner*—Todd E Manahan
*Assistant Examiner*—Erin Colello
(74) *Attorney, Agent, or Firm*—Townsend and Townsend and Crew LLP

(57) ABSTRACT

Medical devices (100) and methods for delivery or implantation of prostheses (106) within hollow body organs and vessels (600) or other luminal anatomy are disclosed. The subject technologies may be used in the treatment of atherosclerosis in stenting procedures or for other purposes.

18 Claims, 30 Drawing Sheets

U.S. PATENT DOCUMENTS

| | | | |
|---|---|---|---|
| 4,733,665 A | 3/1988 | Palmaz | |
| 4,762,128 A | 8/1988 | Rosenbluth | |
| 4,768,507 A | 9/1988 | Fischell et al. | |
| 4,771,773 A | 9/1988 | Kropf | |
| 4,776,337 A | 10/1988 | Palmaz | |
| 4,830,003 A | 5/1989 | Wolff et al. | |
| 4,848,343 A | 7/1989 | Wallsten et al. | |
| 4,875,480 A | 10/1989 | Imbert | |
| 4,878,906 A | 11/1989 | Lindemann et al. | |
| 4,893,623 A | 1/1990 | Rosenbluth | |
| 4,913,141 A | 4/1990 | Hillstead | |
| 4,950,227 A | 8/1990 | Savin et al. | |
| 4,954,126 A | 9/1990 | Wallsten | |
| 4,969,890 A | 11/1990 | Sugita et al. | |
| 4,990,151 A | 2/1991 | Wallsten | |
| 4,990,155 A | 2/1991 | Wilkoff | |
| 4,998,539 A | 3/1991 | Delsanti | |
| 5,019,085 A | 5/1991 | Hillstead | |
| 5,019,090 A | 5/1991 | Pinchuk | |
| 5,026,377 A | 6/1991 | Burton et al. | |
| 5,035,706 A | 7/1991 | Giantureo et al. | |
| 5,061,275 A | 10/1991 | Wallsten et al. | |
| 5,064,435 A | 11/1991 | Porter | |
| 5,067,957 A | 11/1991 | Jervis | |
| 5,071,407 A | 12/1991 | Termin et al. | |
| 5,089,006 A | 2/1992 | Stiles | |
| 5,092,877 A | 3/1992 | Pinchuk | |
| 5,102,417 A | 4/1992 | Palmaz | |
| 5,108,407 A | 4/1992 | Geremia et al. | |
| 5,108,416 A | 4/1992 | Ryan et al. | |
| 5,122,136 A | 6/1992 | Guglielmi | |
| 5,147,370 A | 9/1992 | McNamara et al. | |
| 5,158,548 A | 10/1992 | Lau et al. | |
| 5,180,367 A | 1/1993 | Kontos et al. | |
| 5,192,297 A | 3/1993 | Hull | |
| 5,201,757 A * | 4/1993 | Heyn et al. | 606/198 |
| 5,221,261 A | 6/1993 | Termin et al. | |
| 5,242,399 A | 9/1993 | Lau et al. | |
| 5,242,452 A | 9/1993 | Inoue | |
| 5,246,445 A | 9/1993 | Yachia et al. | |
| 5,263,964 A | 11/1993 | Purdy | |
| 5,266,073 A | 11/1993 | Wall | |
| 5,290,305 A | 3/1994 | Inoue | |
| 5,306,294 A | 4/1994 | Winston et al. | |
| 5,320,635 A | 6/1994 | Smith | |
| 5,334,210 A | 8/1994 | Gianturco | |
| 5,354,295 A | 10/1994 | Guglielmi et al. | |
| 5,360,401 A | 11/1994 | Turnland et al. | |
| 5,372,600 A | 12/1994 | Beyar et al. | |
| 5,382,259 A | 1/1995 | Phelps et al. | |
| 5,407,432 A | 4/1995 | Solar | |
| 5,415,664 A | 5/1995 | Pinchuk | |
| 5,423,829 A | 6/1995 | Pham et al. | |
| 5,433,723 A | 7/1995 | Lindenberg et al. | |
| 5,443,477 A | 8/1995 | Marin et al. | |
| 5,445,646 A | 8/1995 | Euteneuer et al. | |
| 5,476,505 A | 12/1995 | Limon | |
| 5,484,444 A | 1/1996 | Braunschweiler et al. | |
| 5,486,195 A | 1/1996 | Myers et al. | |
| 5,507,771 A | 4/1996 | Gianturco | |
| 5,522,836 A | 6/1996 | Palermo | |
| 5,522,883 A | 6/1996 | Slater et al. | |
| 5,534,007 A | 7/1996 | St. Germain et al. | |
| 5,540,680 A | 7/1996 | Guglielmi et al. | |
| 5,554,181 A | 9/1996 | Das | |
| 5,569,245 A | 10/1996 | Guglielmi et al. | |
| 5,571,135 A | 11/1996 | Fraser et al. | |
| 5,578,074 A | 11/1996 | Mirigian | |
| 5,591,196 A | 1/1997 | Marin et al. | |
| 5,601,600 A | 2/1997 | Ton | |
| 5,618,300 A | 4/1997 | Marin et al. | |
| 5,634,928 A * | 6/1997 | Fischell et al. | 623/1.11 |
| 5,639,274 A * | 6/1997 | Fischell et al. | 604/96.01 |
| 5,643,254 A | 7/1997 | Scheldrup et al. | |
| 5,653,748 A | 8/1997 | Strecker | |
| 5,683,451 A | 11/1997 | Lenker et al. | |
| 5,690,643 A | 11/1997 | Wijay | |
| 5,690,644 A | 11/1997 | Yurek et al. | |
| 5,702,364 A | 12/1997 | Euteneuer et al. | |
| 5,702,418 A | 12/1997 | Ravenscroft | |
| 5,725,549 A | 3/1998 | Lam | |
| 5,725,551 A | 3/1998 | Myers et al. | |
| 5,733,267 A | 3/1998 | Del Toro | |
| 5,733,325 A | 3/1998 | Robinson et al. | |
| 5,772,609 A | 6/1998 | Nguyen et al. | |
| 5,772,668 A | 6/1998 | Summers et al. | |
| 5,772,669 A | 6/1998 | Vrba | |
| 5,776,141 A | 7/1998 | Klein et al. | |
| 5,776,142 A | 7/1998 | Gunderson | |
| 5,782,838 A | 7/1998 | Beyar et al. | |
| 5,788,707 A | 8/1998 | Del Toro et al. | |
| 5,797,857 A | 8/1998 | Obitsu | |
| 5,797,952 A | 8/1998 | Klein | |
| 5,800,455 A | 9/1998 | Palermo et al. | |
| 5,800,517 A | 9/1998 | Anderson et al. | |
| 5,807,398 A | 9/1998 | Shaknovich | |
| 5,810,837 A | 9/1998 | Hofmann et al. | |
| 5,817,101 A | 10/1998 | Fiedler | |
| 5,824,041 A | 10/1998 | Lenker et al. | |
| 5,824,053 A | 10/1998 | Khosravi et al. | |
| 5,824,058 A | 10/1998 | Ravenscroft et al. | |
| RE35,988 E | 12/1998 | Winston et al. | |
| 5,843,090 A * | 12/1998 | Schuetz | 623/1.11 |
| 5,851,206 A | 12/1998 | Guglielmi et al. | |
| 5,855,578 A | 1/1999 | Guglielmi et al. | |
| 5,873,907 A | 2/1999 | Frantzen | |
| 5,891,128 A | 4/1999 | Gia et al. | |
| 5,919,187 A | 7/1999 | Guglielmi et al. | |
| 5,919,204 A | 7/1999 | Lukic et al. | |
| 5,919,225 A | 7/1999 | Lau et al. | |
| 5,920,975 A | 7/1999 | Morales | |
| 5,941,888 A | 8/1999 | Wallace et al. | |
| 5,944,726 A | 8/1999 | Blaeser et al. | |
| 5,948,017 A | 9/1999 | Taheri | |
| 5,957,930 A | 9/1999 | Vrba | |
| 5,968,052 A | 10/1999 | Sullivan et al. | |
| 5,980,485 A | 11/1999 | Grantz et al. | |
| 5,980,514 A | 11/1999 | Kupiecki et al. | |
| 5,980,530 A | 11/1999 | Willard et al. | |
| 5,984,929 A | 11/1999 | Bashiri et al. | |
| 5,989,242 A | 11/1999 | Saadat et al. | |
| 5,989,280 A | 11/1999 | Euteneuer et al. | |
| 6,004,328 A | 12/1999 | Solar | |
| 6,015,429 A | 1/2000 | Lau et al. | |
| 6,019,737 A | 2/2000 | Murata | |
| 6,019,779 A | 2/2000 | Thorud et al. | |
| 6,027,516 A | 2/2000 | Kolobow et al. | |
| 6,027,520 A | 2/2000 | Tsugita et al. | |
| 6,042,588 A | 3/2000 | Munsinger et al. | |
| 6,042,589 A | 3/2000 | Marianne | |
| 6,042,605 A | 3/2000 | Martin et al. | |
| 6,048,360 A | 4/2000 | Khosravi et al. | |
| 6,053,940 A | 4/2000 | Wijay | |
| 6,056,759 A | 5/2000 | Fiedler | |
| 6,059,779 A | 5/2000 | Mills | |
| 6,059,813 A * | 5/2000 | Vrba et al. | 606/198 |
| 6,063,101 A | 5/2000 | Jacobsen et al. | |
| 6,063,104 A | 5/2000 | Villar et al. | |
| 6,068,634 A | 5/2000 | Lorentzen Cornelius et al. | |
| 6,068,644 A | 5/2000 | Lulo et al. | |
| 6,071,286 A | 6/2000 | Mawad | |
| 6,077,297 A | 6/2000 | Robinson et al. | |
| 6,093,194 A | 7/2000 | Mikus et al. | |
| 6,096,034 A | 8/2000 | Kupiecki et al. | |

| | | | |
|---|---|---|---|
| 6,096,045 A | 8/2000 | Del Toro et al. | |
| 6,102,942 A | 8/2000 | Ahari | |
| 6,113,608 A | 9/2000 | Monroe et al. | |
| 6,117,140 A | 9/2000 | Munsinger | |
| 6,120,522 A | 9/2000 | Vrba et al. | |
| 6,123,714 A | 9/2000 | Gia et al. | |
| 6,123,720 A | 9/2000 | Anderson et al. | |
| 6,126,685 A | 10/2000 | Lenker et al. | |
| 6,139,524 A | 10/2000 | Killion | |
| 6,139,564 A | 10/2000 | Teoh | |
| 6,156,061 A | 12/2000 | Wallace et al. | |
| 6,156,062 A | 12/2000 | McGuinness | |
| 6,161,029 A | 12/2000 | Spreigl et al. | |
| 6,165,178 A | 12/2000 | Bashiri et al. | |
| 6,168,579 B1 | 1/2001 | Tsugita | |
| 6,168,592 B1 | 1/2001 | Kupiecki et al. | |
| 6,168,616 B1 | 1/2001 | Brown, III | |
| 6,168,618 B1 | 1/2001 | Frantzen | |
| 6,174,327 B1 | 1/2001 | Mertens et al. | |
| 6,183,481 B1 | 2/2001 | Lee et al. | |
| 6,183,505 B1 | 2/2001 | Mohn, Jr. et al. | |
| 6,200,305 B1 | 3/2001 | Berthiaume et al. | |
| 6,203,550 B1 | 3/2001 | Olson | |
| 6,206,888 B1 | 3/2001 | Bicek et al. | |
| 6,214,036 B1 | 4/2001 | Letendre et al. | |
| 6,221,081 B1 | 4/2001 | Mikus et al. | |
| 6,221,097 B1 | 4/2001 | Wang et al. | |
| 6,228,110 B1 | 5/2001 | Munsinger | |
| 6,238,410 B1 * | 5/2001 | Vrba et al. | 606/198 |
| 6,238,430 B1 | 5/2001 | Klumb et al. | |
| 6,241,758 B1 | 6/2001 | Cox | |
| 6,245,097 B1 | 6/2001 | Inoue | |
| 6,248,122 B1 | 6/2001 | Klumb et al. | |
| 6,254,609 B1 | 7/2001 | Vrba et al. | |
| 6,254,611 B1 | 7/2001 | Vrba | |
| 6,254,628 B1 | 7/2001 | Wallace et al. | |
| 6,264,671 B1 * | 7/2001 | Stack et al. | 606/198 |
| 6,264,683 B1 | 7/2001 | Stack et al. | |
| 6,267,783 B1 | 7/2001 | Letendre et al. | |
| 6,270,504 B1 | 8/2001 | Lorentzen Cornelius et al. | |
| 6,273,881 B1 | 8/2001 | Kiemeneij | |
| 6,280,465 B1 | 8/2001 | Cryer | |
| 6,287,331 B1 | 9/2001 | Heath | |
| 6,302,893 B1 | 10/2001 | Limon et al. | |
| 6,306,141 B1 | 10/2001 | Jervis | |
| 6,306,162 B1 * | 10/2001 | Patel | 623/1.11 |
| 6,319,275 B1 * | 11/2001 | Lashinski et al. | 623/1.11 |
| 6,342,066 B1 | 1/2002 | Toro et al. | |
| 6,344,041 B1 | 2/2002 | Kupiecki et al. | |
| 6,346,118 B1 | 2/2002 | Baker et al. | |
| 6,350,277 B1 | 2/2002 | Kocur | |
| 6,350,278 B1 | 2/2002 | Lenker et al. | |
| 6,361,637 B2 | 3/2002 | Martin et al. | |
| 6,368,344 B1 | 4/2002 | Fitz | |
| 6,371,962 B1 | 4/2002 | Ellis et al. | |
| 6,375,660 B1 | 4/2002 | Fischell et al. | |
| 6,379,365 B1 | 4/2002 | Diaz | |
| 6,380,457 B1 | 4/2002 | Yurek et al. | |
| 6,383,174 B1 | 5/2002 | Eder | |
| 6,387,118 B1 | 5/2002 | Hanson | |
| 6,391,050 B1 | 5/2002 | Broome | |
| 6,391,051 B2 | 5/2002 | Sullivan, III et al. | |
| 6,395,017 B1 | 5/2002 | Dwyer et al. | |
| 6,409,750 B1 | 6/2002 | Hyodoh et al. | |
| 6,409,752 B1 | 6/2002 | Boatman et al. | |
| 6,413,269 B1 | 7/2002 | Bui et al. | |
| 6,416,536 B1 | 7/2002 | Yee | |
| 6,416,545 B1 | 7/2002 | Mikus et al. | |
| 6,423,090 B1 | 7/2002 | Hancock | |
| 6,425,898 B1 | 7/2002 | Wilson et al. | |
| 6,425,914 B1 | 7/2002 | Wallace et al. | |
| 6,425,915 B1 | 7/2002 | Khosravi et al. | |
| 6,428,489 B1 | 8/2002 | Jacobsen et al. | |
| 6,428,566 B1 | 8/2002 | Holt | |
| 6,432,080 B2 | 8/2002 | Pederson, Jr. et al. | |
| 6,432,129 B2 | 8/2002 | DiCaprio | |
| 6,447,540 B1 | 9/2002 | Fontaine et al. | |
| 6,448,700 B1 | 9/2002 | Gupta et al. | |
| 6,451,025 B1 | 9/2002 | Jervis | |
| 6,451,052 B1 | 9/2002 | Burmeister et al. | |
| 6,454,795 B1 | 9/2002 | Chuter | |
| 6,458,092 B1 | 10/2002 | Gambale et al. | |
| 6,468,266 B1 | 10/2002 | Bashiri et al. | |
| 6,468,298 B1 | 10/2002 | Pelton | |
| 6,468,301 B1 | 10/2002 | Amplatz et al. | |
| 6,482,227 B1 | 11/2002 | Solovay | |
| 6,485,515 B2 | 11/2002 | Strecker | |
| 6,488,700 B2 | 12/2002 | Klumb et al. | |
| 6,517,548 B2 | 2/2003 | Lorentzen Cornelius et al. | |
| 6,517,569 B2 | 2/2003 | Mikus et al. | |
| 6,520,986 B2 | 2/2003 | Martin et al. | |
| 6,530,947 B1 | 3/2003 | Euteneuer et al. | |
| 6,533,805 B1 | 3/2003 | Jervis | |
| 6,533,807 B2 | 3/2003 | Wolinsky et al. | |
| 6,537,295 B2 | 3/2003 | Petersen | |
| 6,558,415 B2 | 5/2003 | Thompson | |
| 6,562,063 B1 | 5/2003 | Euteneuer et al. | |
| 6,562,064 B1 | 5/2003 | deBeer | |
| 6,579,297 B2 | 6/2003 | Bicek et al. | |
| 6,579,308 B1 | 6/2003 | Jansen et al. | |
| 6,582,460 B1 | 6/2003 | Cryer | |
| 6,602,226 B1 | 8/2003 | Smith et al. | |
| 6,602,272 B2 | 8/2003 | Boylan et al. | |
| 6,607,539 B1 | 8/2003 | Hayashi et al. | |
| 6,607,551 B1 | 8/2003 | Sullivan et al. | |
| 6,613,079 B1 | 9/2003 | Wolinsky et al. | |
| 6,620,152 B2 | 9/2003 | Guglielmi | |
| 6,623,518 B2 | 9/2003 | Thompson et al. | |
| 6,626,938 B1 | 9/2003 | Butaric et al. | |
| 6,629,981 B2 | 10/2003 | Bui et al. | |
| 6,645,237 B2 | 11/2003 | Klumb et al. | |
| 6,645,238 B2 | 11/2003 | Smith | |
| 6,656,212 B2 | 12/2003 | Ravenscroft et al. | |
| 6,660,031 B2 | 12/2003 | Tran et al. | |
| 6,660,032 B2 | 12/2003 | Klumb et al. | |
| 6,663,660 B2 | 12/2003 | Dusbabek et al. | |
| 6,666,881 B1 | 12/2003 | Richter et al. | |
| 6,669,719 B2 | 12/2003 | Wallace et al. | |
| 6,676,666 B2 | 1/2004 | Vrba et al. | |
| 6,679,910 B1 | 1/2004 | Granada | |
| 6,689,120 B1 | 2/2004 | Gerdts | |
| 6,692,521 B2 | 2/2004 | Pinchasik | |
| 6,699,274 B2 | 3/2004 | Stinson | |
| 6,702,843 B1 * | 3/2004 | Brown et al. | 623/1.11 |
| 6,702,846 B2 | 3/2004 | Mikus et al. | |
| 6,709,425 B2 | 3/2004 | Gambale et al. | |
| 6,716,238 B2 | 4/2004 | Elliott | |
| 6,726,714 B2 | 4/2004 | DiCaprio et al. | |
| 6,733,519 B2 * | 5/2004 | Lashinski et al. | 623/1.11 |
| 6,736,839 B2 | 5/2004 | Cummings | |
| 6,802,858 B2 | 10/2004 | Gambale et al. | |
| 6,814,746 B2 | 11/2004 | Thompson et al. | |
| 6,818,014 B2 | 11/2004 | Brown et al. | |
| 6,830,575 B2 | 12/2004 | Stenzel et al. | |
| 6,833,002 B2 * | 12/2004 | Stack et al. | 623/1.11 |
| 6,833,003 B2 | 12/2004 | Jones et al. | |
| 6,843,802 B1 | 1/2005 | Villalobos et al. | |
| 6,858,034 B1 | 2/2005 | Hijlkema et al. | |
| 6,860,899 B1 | 3/2005 | Rivelli, Jr. | |
| 6,875,212 B2 | 4/2005 | Shaolian et al. | |
| 6,936,058 B2 | 8/2005 | Forde et al. | |
| 6,936,065 B2 | 8/2005 | Khan et al. | |
| 6,989,024 B2 | 1/2006 | Hebert et al. | |
| 7,011,673 B2 | 3/2006 | Fischell et al. | |
| 7,074,236 B2 | 7/2006 | Rabkin et al. | |
| 7,172,620 B2 | 2/2007 | Gilson | |

| | | |
|---|---|---|
| 7,300,460 B2 | 11/2007 | Levine et al. |
| 7,393,357 B2 | 7/2008 | Stelter et al. |
| 2001/0034548 A1 | 10/2001 | Vrba et al. |
| 2001/0047185 A1 | 11/2001 | Satz |
| 2001/0049547 A1 | 12/2001 | Moore |
| 2001/0049550 A1 | 12/2001 | Martin et al. |
| 2002/0002397 A1 | 1/2002 | Martin et al. |
| 2002/0032431 A1 | 3/2002 | Kiemeneij |
| 2002/0035393 A1* | 3/2002 | Lashinski et al. .......... 623/1.11 |
| 2002/0040236 A1 | 4/2002 | Lau et al. |
| 2002/0045928 A1 | 4/2002 | Boekstegers |
| 2002/0045930 A1 | 4/2002 | Burg et al. |
| 2002/0049490 A1 | 4/2002 | Pollock et al. |
| 2002/0068966 A1 | 6/2002 | Holman et al. |
| 2002/0072729 A1 | 6/2002 | Hoste et al. |
| 2002/0077693 A1 | 6/2002 | Barclay et al. |
| 2002/0095147 A1 | 7/2002 | Shadduck |
| 2002/0095168 A1 | 7/2002 | Griego et al. |
| 2002/0099433 A1 | 7/2002 | Fischell et al. |
| 2002/0120322 A1 | 8/2002 | Thompson et al. |
| 2002/0120323 A1 | 8/2002 | Thompson |
| 2002/0120324 A1 | 8/2002 | Holman et al. |
| 2002/0138129 A1 | 9/2002 | Armstrong et al. |
| 2002/0147491 A1 | 10/2002 | Khan et al. |
| 2002/0161342 A1 | 10/2002 | Rivelli et al. |
| 2002/0169494 A1 | 11/2002 | Mertens et al. |
| 2002/0188341 A1 | 12/2002 | Elliott et al. |
| 2003/0014103 A1 | 1/2003 | Inoue |
| 2003/0018319 A1 | 1/2003 | Kiemeneij |
| 2003/0036768 A1 | 2/2003 | Hutchins et al. |
| 2003/0040771 A1 | 2/2003 | Hyodoh et al. |
| 2003/0040772 A1 | 2/2003 | Hyodoh et al. |
| 2003/0055377 A1 | 3/2003 | Sirhan et al. |
| 2003/0065375 A1 | 4/2003 | Eskuri |
| 2003/0069521 A1 | 4/2003 | Reynolds et al. |
| 2003/0105508 A1 | 6/2003 | Johnson et al. |
| 2003/0135266 A1 | 7/2003 | Chew et al. |
| 2003/0149467 A1 | 8/2003 | Linder et al. |
| 2003/0163156 A1* | 8/2003 | Herbert et al. .............. 606/194 |
| 2003/0163189 A1* | 8/2003 | Thompson et al. ......... 623/1.11 |
| 2004/0010265 A1 | 1/2004 | Karpiel |
| 2004/0049547 A1 | 3/2004 | Matthews et al. |
| 2004/0093063 A1 | 5/2004 | Wright et al. |
| 2004/0097917 A1 | 5/2004 | Keane |
| 2004/0127912 A1 | 7/2004 | Rabkin et al. |
| 2004/0193178 A1 | 9/2004 | Nikolchev |
| 2004/0193179 A1 | 9/2004 | Nikolchev |
| 2004/0193246 A1 | 9/2004 | Ferrera |
| 2004/0220585 A1 | 11/2004 | Nikolchev |
| 2004/0260377 A1 | 12/2004 | Flomenblit et al. |
| 2005/0049668 A1* | 3/2005 | Jones et al. |
| 2005/0049669 A1* | 3/2005 | Jones et al. ................ 623/1.12 |
| 2005/0049670 A1* | 3/2005 | Jones et al. ................ 623/1.12 |
| 2005/0080430 A1 | 4/2005 | Wright, Jr. et al. |
| 2005/0096724 A1 | 5/2005 | Stenzel et al. |
| 2005/0209670 A1 | 9/2005 | George et al. |
| 2005/0209671 A1 | 9/2005 | Ton et al. |
| 2005/0209672 A1 | 9/2005 | George et al. |
| 2005/0209675 A1 | 9/2005 | Ton et al. |
| 2005/0220836 A1 | 10/2005 | Falotico et al. |
| 2006/0085057 A1 | 4/2006 | George et al. |
| 2006/0111771 A1 | 5/2006 | Ton et al. |
| 2006/0136037 A1 | 6/2006 | DeBeer et al. |
| 2006/0247661 A1 | 11/2006 | Richards et al. |
| 2006/0270948 A1 | 11/2006 | Viswanathan et al. |
| 2006/0271097 A1 | 11/2006 | Ramzipoor et al. |
| 2006/0276886 A1 | 12/2006 | George et al. |
| 2007/0027522 A1 | 2/2007 | Chang et al. |
| 2007/0073379 A1 | 3/2007 | Chang et al. |
| 2007/0100414 A1 | 5/2007 | Licata et al. |
| 2007/0100415 A1 | 5/2007 | Licata et al. |
| 2007/0100416 A1 | 5/2007 | Licata |
| 2007/0100417 A1 | 5/2007 | Licata |
| 2007/0100418 A1 | 5/2007 | Licata |
| 2008/0015541 A1 | 1/2008 | Rosenbluth et al. |
| 2008/0071309 A1 | 3/2008 | Mazzocchi et al. |
| 2008/0221666 A1 | 9/2008 | Licata et al. |

FOREIGN PATENT DOCUMENTS

| | | |
|---|---|---|
| EP | 0667 132 | 8/1995 |
| EP | 0 747 021 | 12/1996 |
| EP | 1 157 673 | 11/2001 |
| EP | 1 518 515 | 3/2005 |
| EP | 1 518 515 A1 | 3/2005 |
| EP | 1518515 A1 * | 3/2005 |
| JP | 2002-538938 | 11/2002 |
| WO | WO 97/12563 | 4/1997 |
| WO | WO 97/48343 | 12/1997 |
| WO | WO 98/23241 | 6/1998 |
| WO | WO 99/04728 | 2/1999 |
| WO | WO 99/08740 | 2/1999 |
| WO | WO 00/18330 | 4/2000 |
| WO | WO 00/56248 | 9/2000 |
| WO | WO 01/78627 A1 | 10/2001 |
| WO | WO 0178627 A1 * | 10/2001 |
| WO | WO 03/073963 | 9/2003 |
| WO | WO 2004/087006 | 10/2004 |
| WO | WO 2005/092241 | 10/2005 |
| WO | WO 2005/094727 | 10/2005 |

OTHER PUBLICATIONS

Duerig et al., "An overview of superelastic stent desing" Min Invas Ther & Allied Technol, 9(3/4):234-246 (2000).

Kandzari et al. "Clinical and Angiographic Efficacy of a Self-Expanding Nitinol Stent in Saphenous Vein Graft Atherschlerotic Disease" Am. Heart J 145(5):868-874 (2003).

Rieu et al., Radial Force of Coronary Stents; A Comparative Analysis: Catheterization and Cardiovascular Interventions 46:380-391 (1999).

Schuessler et al. Stent Materials and Manufacturing: Requirements and Possibilities/Opportunities, ASM Materials & Processes, Anaheim, CA. (Sep. 8-10, 2003).

Stoeckel et al. "A Survey of Stent Desings" Min Invas Ther & Allied Technol 11(4):137-147(2002).

Welt et al. "Coronary Artery Stents: Design and Biologic Considerations" Cardiology Special Edition 9(2) 9-14(2003).

Bonsignore, Craig, "A Decade of Evolution in Stent Design" Cordis Corporation Nitinol Devices & Components. 47533 Westinqhouse Drive, Fremont. California 94539.

Fischell, M.D. FACC, Tim A.. "A Fixed Guidewire Stent Delivery System Rationale and Design" TCT. Washington. D.C. (Sep. 24, 2002).

Poncet, Philippe P., "Nitinol Medical Device Design Considerations" Memry Corporation. 4065 Campbell Avenue, Menlo Park. California 94025. pp. 1-12.

Schuessler et al., Stent Materials and Manufacturing: Requirements and Possibilities/Opportunities, ASM Materials & Processes for Medical Devices, Anaheim, CA. (Sep. 8-10, 2003).

Welt et al. "Coronary Artery Stents: Design and Biologic Considerations" Cardiology Special Edition 9(2) 9-14(2003).

Rogers, C. "DES Overview: Agents: release mechanism and stent platform", PowerPoint Presentation, 51 pages total.

Definitions of "abut" and "wire"—Random House College Dictionary, 1980, New York, 7 and 510.

International Search Report and Written Opinion of PCT Application No. PCT/US2004/008909, mailed Sep. 24, 2004, 6 pages total.

Office Action of Japanese Application No. 2006-507500, mailed Nov. 18, 2009, 9 pages. (including English Translation).

Examination Report of Singaporean Application No. 2005050976-1, mailed Feb. 28, 2007, 10 pages total.

Written Opinion of Singaporean Application No. 2005050976-1, mailed Apr. 27, 2006, 9 pages total.

Examination Report of Australian Application No. 2004226464, mailed Jul. 17, 2007, 2 pages total.

International Search Report of PCT Application No. PCT/US2006/34130, mailed Nov. 23, 2007, 8 pages total.

International Preliminary Report on Patentability of PCT Application No. PCT/US2006/34130, dated Oct. 14, 2008, 8 pages total.

* cited by examiner

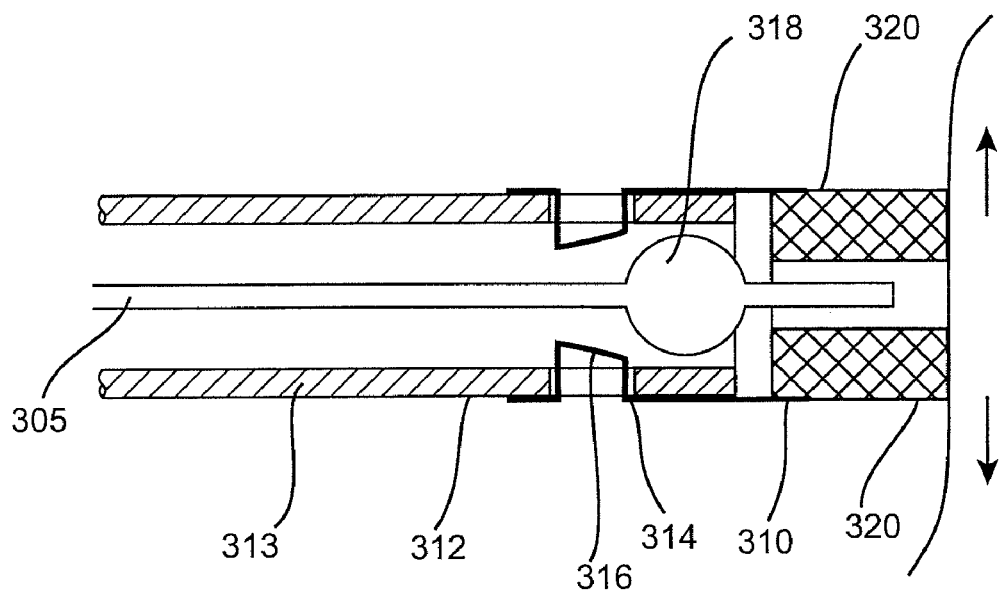
FIG. 3C₁
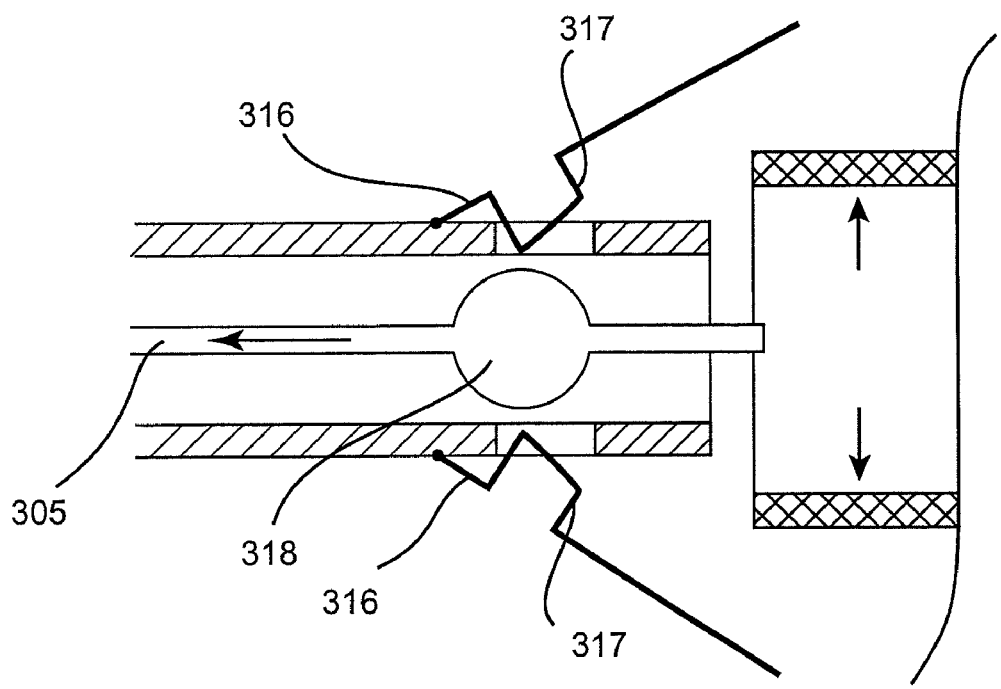
FIG. 3C₂

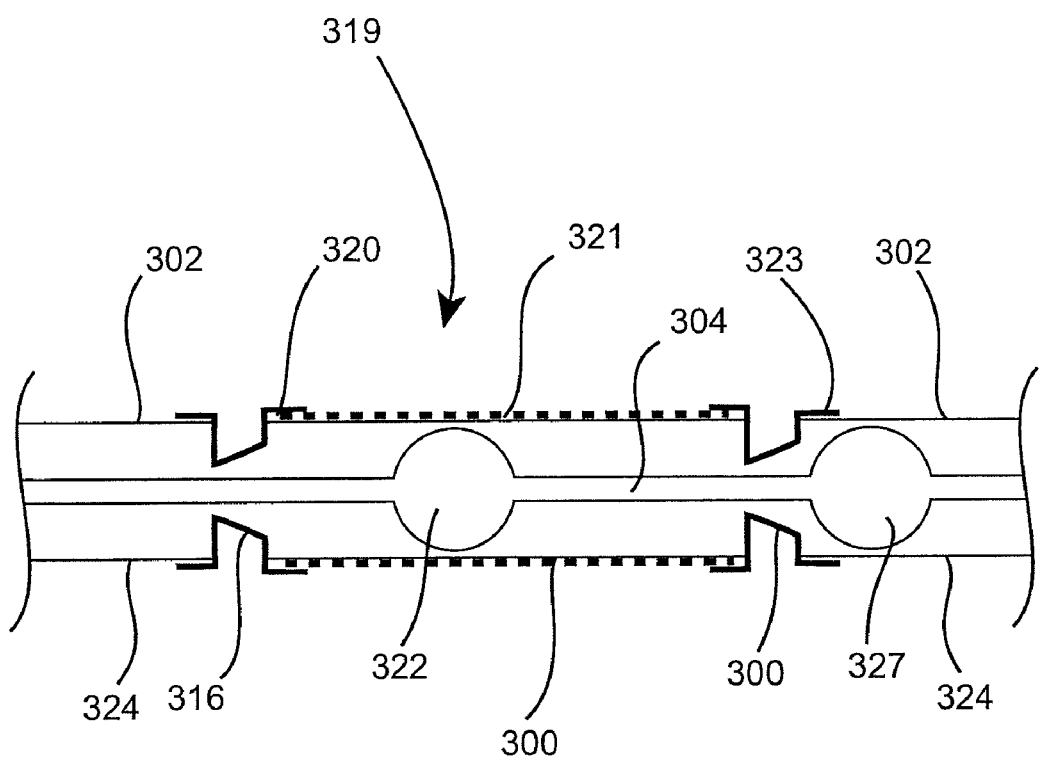
FIG. 3D₁

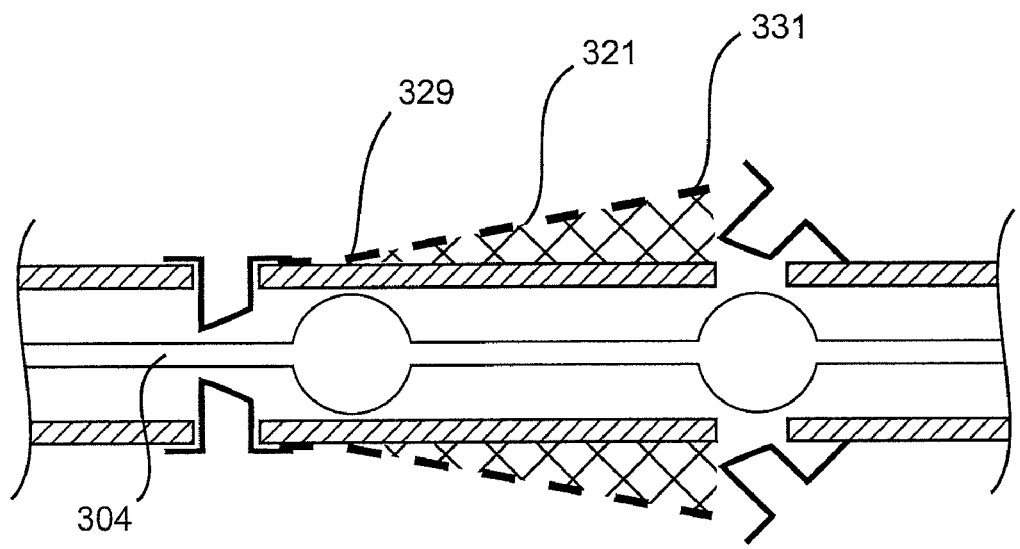
FIG. 3D₂
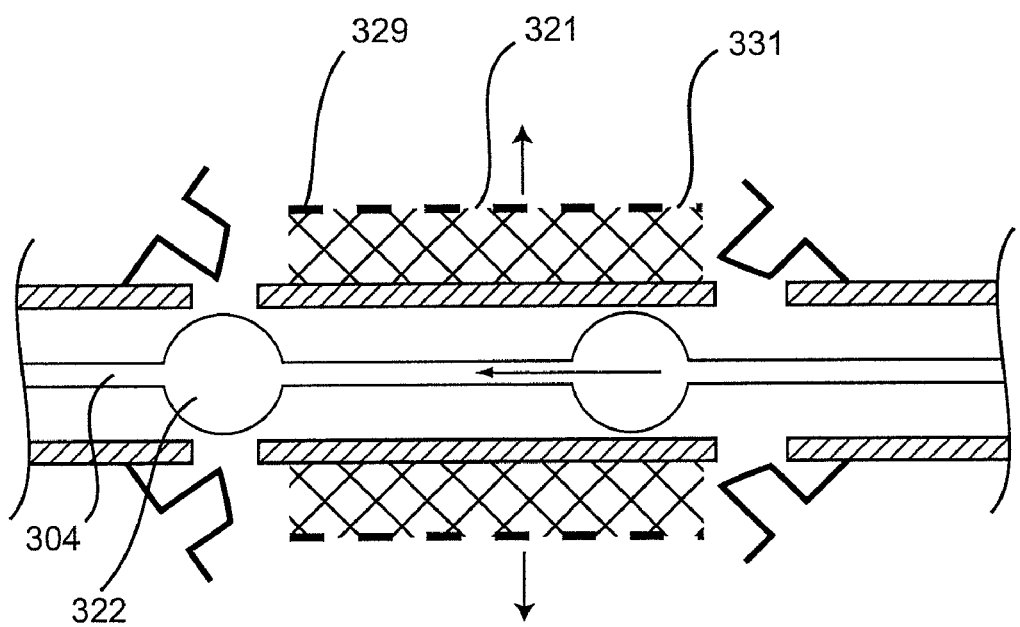
FIG. 3D₃

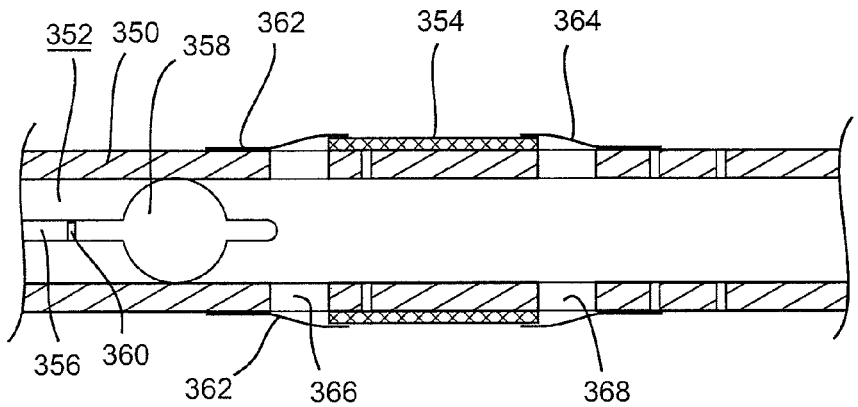
FIG. 3E₁
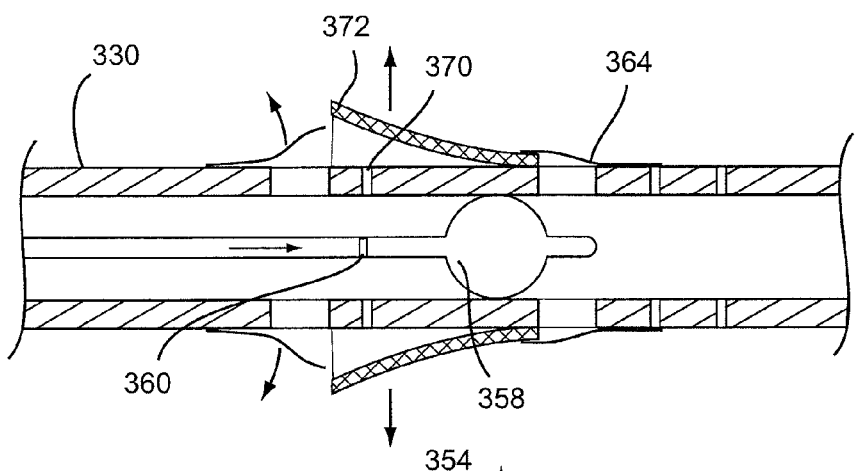
FIG. 3E₂
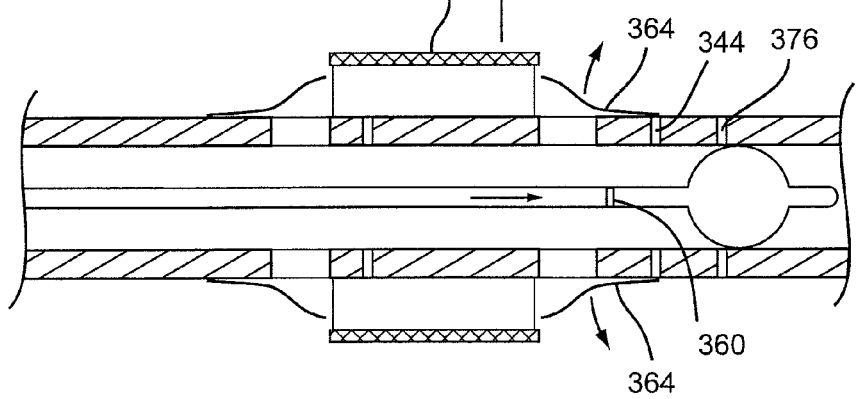
FIG. 3E₃
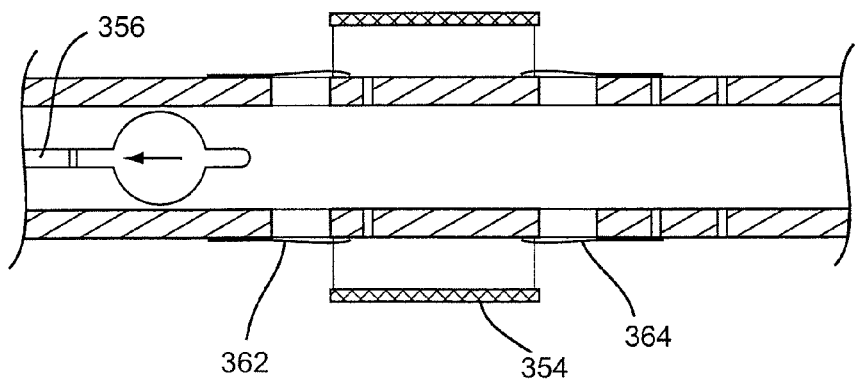
FIG. 3E₄

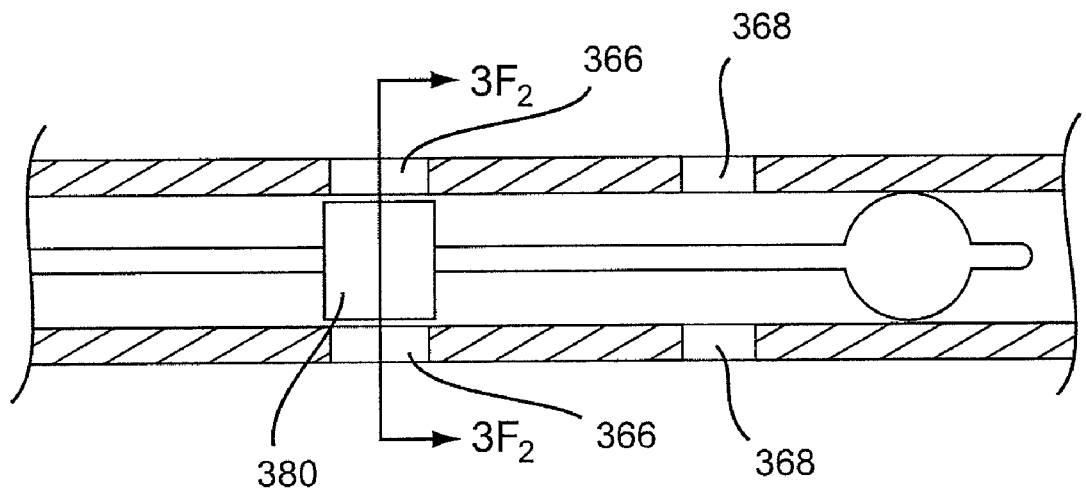
FIG. 3F₁
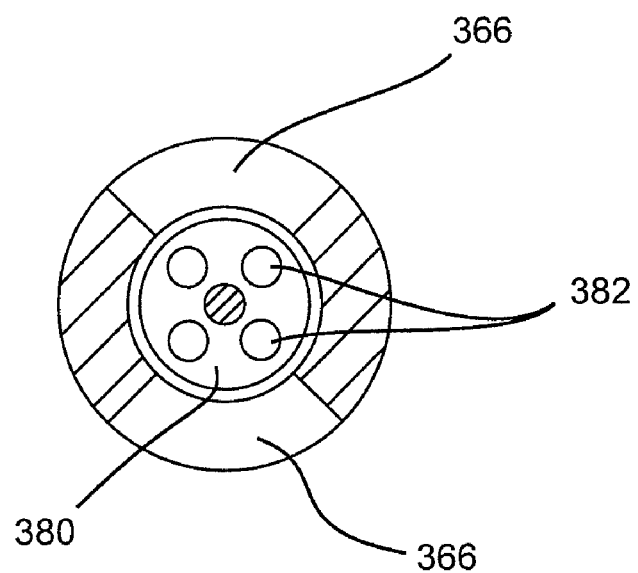
FIG. 3F₂

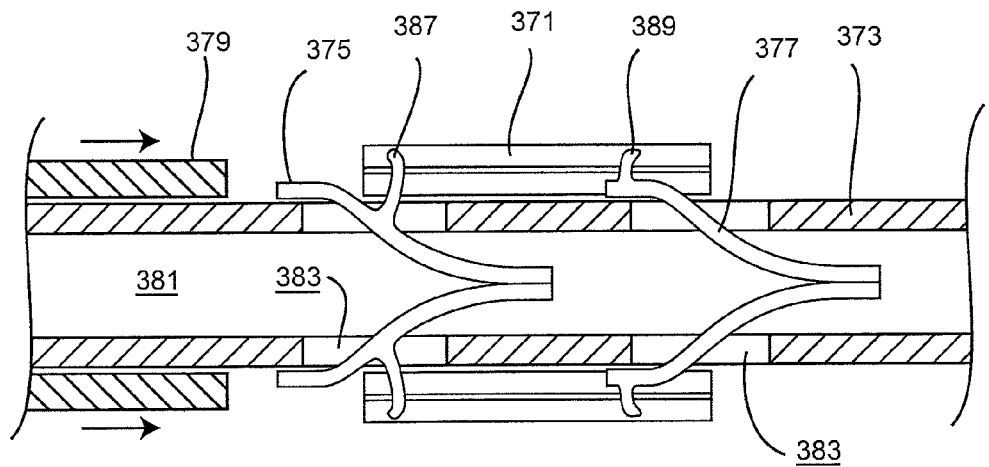
FIG. 3G₁
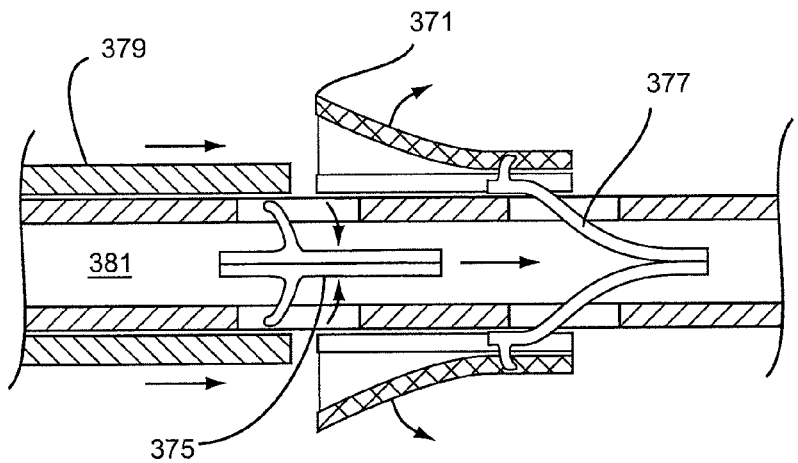
FIG. 3G₂
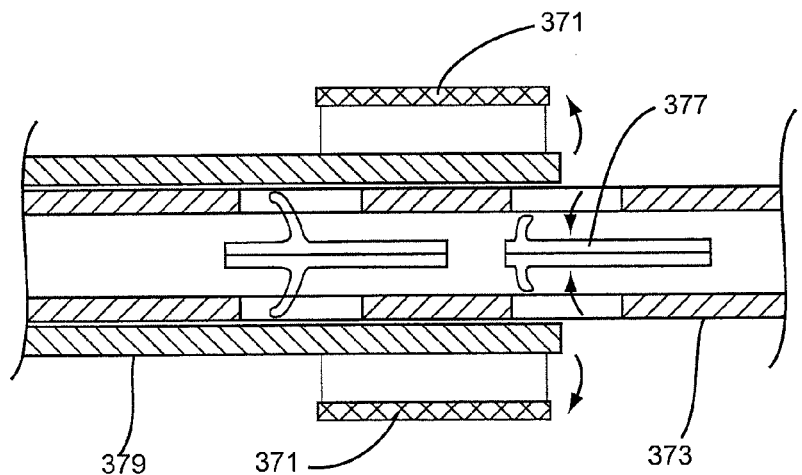
FIG. 3G₃

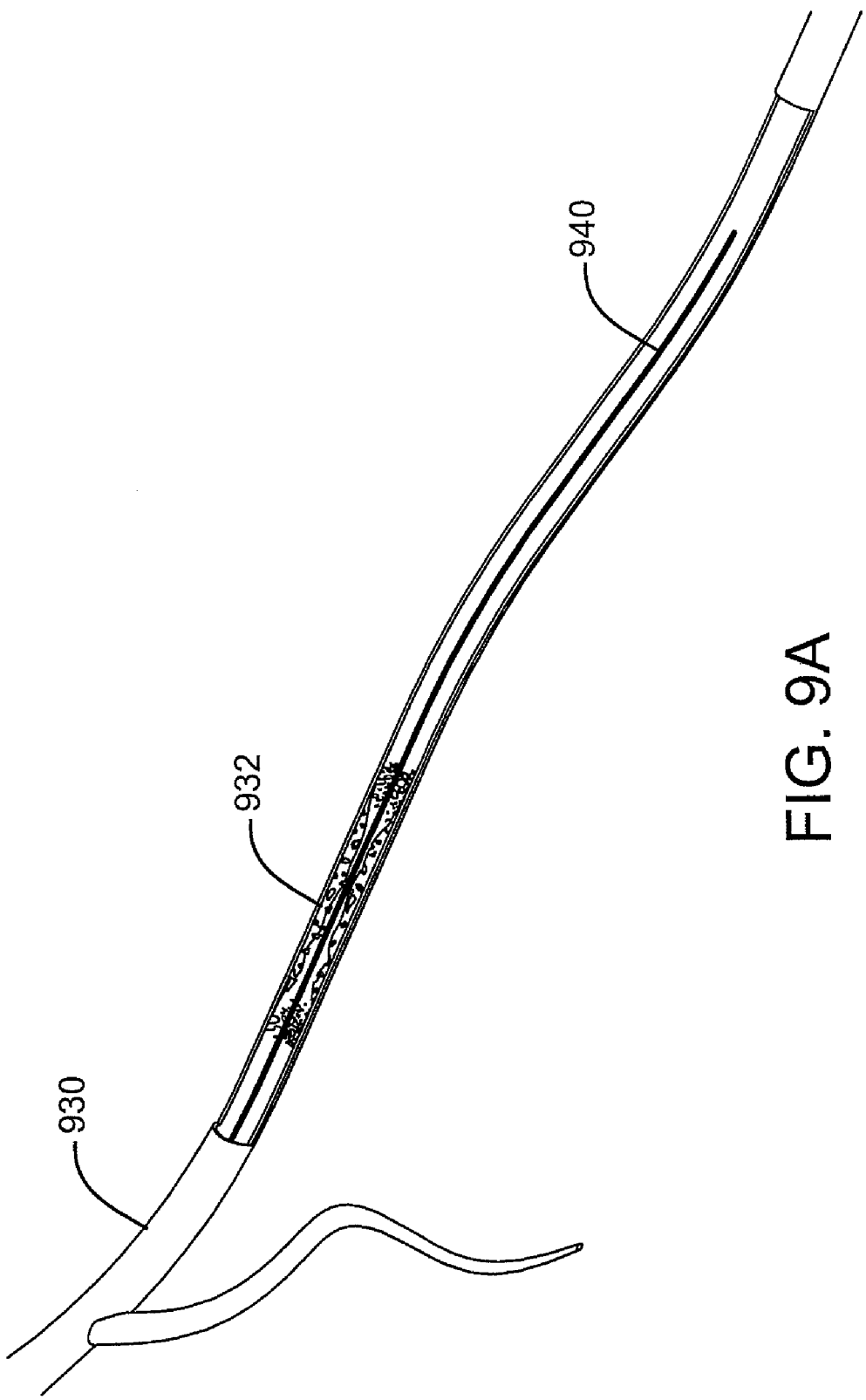

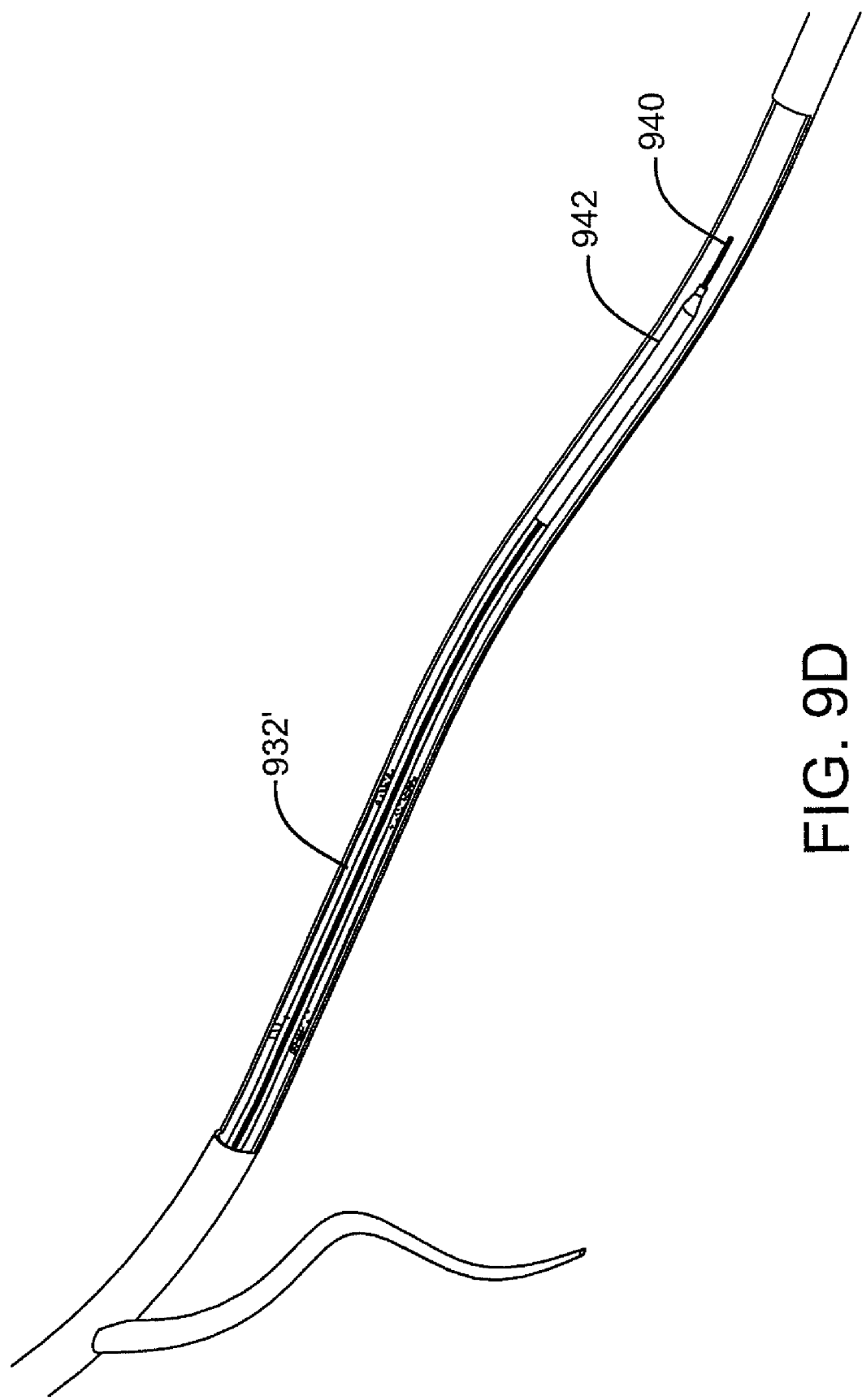

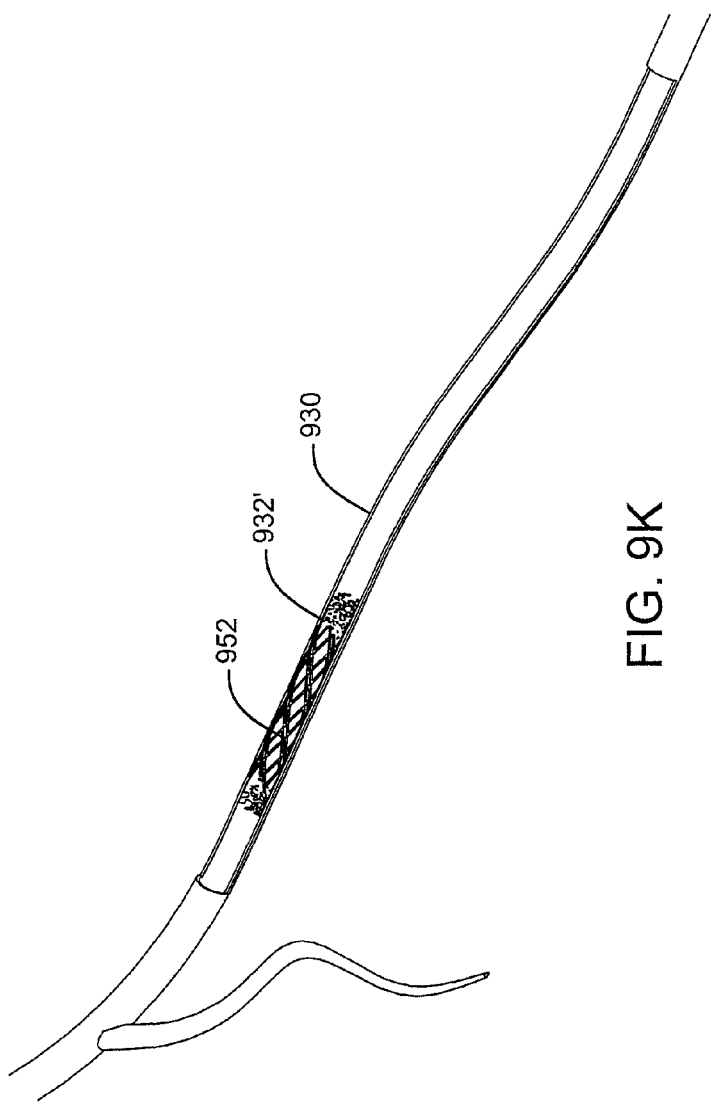
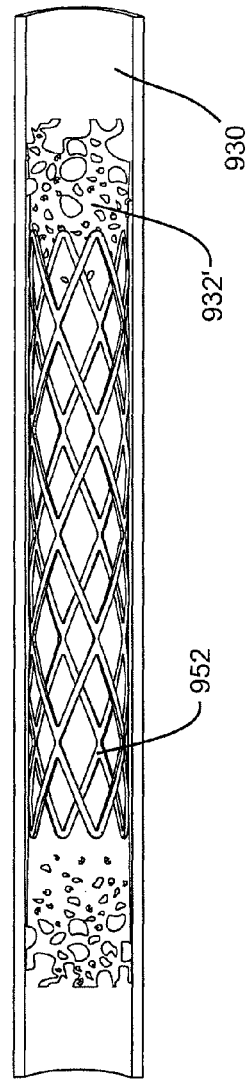
FIG. 9K
FIG. 9L

IMPLANT DELIVERY TECHNOLOGIES

CROSS REFERENCE TO RELATED APPLICATIONS

Priority to or the benefit of U.S. Provisional Patent Applications IMPLANT DELIVERY DEVICE (Ser. No. 60/458,323), filed Mar. 26, 2003 and IMPLANT DELIVERY DEVICE II (Ser. No. 60/462,219), filed Apr. 10, 2003 and U.S. Patent Applications IMPLANT DELIVERY TECHNOLOGIES (Ser. No. 10/745,778), MULTIPLE JOINT IMPLANT DELIVERY SYSTEMS FOR SEQUENTIALLY-CONTROLLED IMPLANT DEPLOYMENT (Ser. No. 10/746,452), and BALLOON CATHETER LUMEN BASED STENT DELIVERY SYSTEMS (Ser. No. 10/746,455), each filed Dec. 24, 2003, and SLIDING RESTRAINT STENT DELIVERY SYSTEMS (Ser. No. 10/792,684), now abandoned filed Mar. 2, 2004 is claimed. Furthermore, each of the above-referenced applications is hereby incorporated by reference herein in its entirety.

FIELD OF THE INVENTION

The present invention relates generally to medical device and methods. More particularly, it relates to delivery systems for implanting prostheses within hollow body organs and vessels or other luminal anatomy.

BACKGROUND OF THE INVENTION

Implants such as stents and occlusive coils have been used in patients for a wide variety of reasons. For instance, stents are often used to treat arterial stenosis secondary to atherosclerosis. Various stent designs have been developed and used clinically, but self-expandable and balloon-expandable stent systems and their related deployment techniques are now predominant. Examples of self-expandable stents currently in use are WALLSTENT® stents and Radius stents (Boston Scientific). A commonly used balloon-expandable stent is the Cypher® stent (Cordis Corporation). Additional self-expanding stent background is presented in: "An Overview of Superelastic Stent Design," Min. Invas Ther & Allied Technol 2002: 9(3/4) 235-246, "A Survey of Stent Designs," Min. Invas Ther & Allied Technol 2002: 11(4) 137-147, and "Coronary Artery Stents: Design and Biologic Considerations," Cardiology Special Edition, 2003: 9(2) 9-14, "Clinical and Angiographic Efficacy of a Self-Expanding Stent" Am Heart J 2003: 145(5) 868-874.

Typically, after balloon angioplasty has been performed, either a self-expandable or balloon-expandable stent is advanced over a guidewire and positioned at the target site. A protective sheath or membrane is then retracted proximally to allow expansion of a self-expanding stent. Alternatively, a delivery balloon may be inflated, thereby expanding the stent.

Despite improvements in delivery systems, balloon design, and stent design, these over-the-guidewire and/or sheathed self-expanding stent deployment systems still have their limitations. For instance, sheathed stents tend to move forward when the sheath is pulled back, deploying them imprecisely. The sheathed design also requires that the stent delivery system be larger in diameter and less flexible. Furthermore, for sheathed systems, the interventional procedure may only proceed if the vessel of interest is of sufficiently large diameter to allow sheath placement to avoid significant damage to the luminal surface of the vessel. Moreover, balloon-expandable stents, by virtue of a large diameter and relative inflexibility, are often unable to reach distal vasculature. For both self-expandable and balloon-expandable stent deployment systems, repositioning or step-wise release of the stent are usually not available features. Similarly, occlusive coil placement systems such as systems that deliver detachable platinum coils and GDC® coils also generally do not contain repositionable or step-wise release features.

Consequently, a smaller diameter (lower profile), repositionable implant deployment device that releases an implant into, or upon, a body region in a more precise, continuous or step-wise fashion, without the use of a sheath or balloon would provide significant benefit to patients with various medical conditions.

SUMMARY OF THE INVENTION

The present invention is a low profile implant delivery device that may be deployed without a sheath, and is designed to release portions of implants simultaneously or sequentially. The invention relates to devices and methods for placing one or more implants such as helical scaffolds or occlusive members into tubular organs or open regions of the body. The implants may be of types that maintain patency of an open anatomical structure, occlude a selected volume, isolate a region, or collect other occlusive members at a site. The invention optionally provides an atraumatic, low profile device for the delivery of one or more implants into tubular organs or open regions of the body. The implant delivery device may simultaneously or independently (e.g., sequentially) release portions of the implant, e.g., the proximal and distal ends of the implant. This independent release feature allows better implant positioning at the target site. Included in the description are devices and methods for deploying the various implants, typically without a sheath, in a serial fashion, and with high adjustability. However, a number of highly space-efficient or otherwise advantageous sheath-based delivery systems are disclosed.

In one variation, the implant delivery device includes a noninflatable, elongate delivery guide member having a distal end and configuration that allows it to direct at least one implant having an exterior and interior surface to an anatomical treatment site by manipulation by a user. The at least one implant has a delivery diameter prior to its release, is located proximally of the distal end of the delivery guide member prior to release, and has at least one releasable joint configured to maintain at least a section of the at least one implant at the delivery diameter until release of the at least one releasable joint. The delivery guide member sections that are proximal and distal to the at least one implant also have delivery diameters. These guide member delivery diameters may be substantially equal to the at least one implant delivery diameter prior to implant release.

The implant may be a helical scaffold, e.g., a stent, in particular, a self-expandable stent, or it may be an occlusive coil. The implant may be symmetric or asymmetric. In some instances, the implant delivers a therapeutic agent.

The delivery guide member may include a wire and/or a tubular member having a lumen. If desired, a radioopaque marker may be included on the delivery guide to aid with its placement. When designed to include a tubular member, it co-axially surrounds at least a portion of the delivery guide, and works as a tubular actuator configured to release at least one releasable joint upon distal axial movement along the delivery guide member.

In another variation, the implant delivery device includes an actuator slidably located at least partially within the delivery guide member and is configured to mechanically release at least one releasable joint upon axial movement of the actuator within the delivery guide member. In other variations, the actuator may also release at least one releasable joint upon rotational movement of the actuator, upon the application of fluid pressure in the delivery guide member lumen, or upon application of a suitable DC current to the at least one releasable joint. Release of the releasable joints using any one of the release mechanisms described above may be sequential, if precise positioning is required, or may be simultaneous.

Other variations of the invention include sheath based delivery systems. In one of these, the core member carrying the stent further included an atraumatic tip. In another, the sheath restraining the stent takes the form of a balloon catheter. In addition, both features may be combined. Additional variations of the invention employ non-active members (in the forms of hooks, grippers, etc.) adapted to interface with a radially expandable implant to pull and/or twist the member in order to hold it in a collapsed configuration.

The implant delivery device may be included in a system for implant delivery which further employs one or more embolic filters at either the proximal or distal section of the delivery guide, or at both the proximal and distal sections of the delivery guide. It may be provided in a kit packaged for sale, together with instructions.

The system may be used for implant delivery into lumens of tubular organs including, but not limited to, blood vessels (including intracranial vessels, large vessels, peripheral vessels, adjacent aneurysms, arteriovenous malformations, arteriovenous fistulas), ureters, bile ducts, fallopian tubes, cardiac chambers, ducts such as bile ducts and mammary ducts, large and small airways, and hollow organs, e.g., stomach, intestines, and bladder. The implant may be of a design that is of a size that is smaller during delivery and larger after implantation. The design may be used to provide or to maintain patency in an open region of an anatomical structure, or to occlude a site, or to isolate a region (e.g., to close an aneurysm by blocking the aneurysm opening or neck by placement in an adjacent anatomical structure such as an artery or gastrointesinal tubular member), or to corral or collect a number of occlusive devices (e.g., coils or hydratable polymeric noodles) or compositions at a site to be occluded or supported. In another variation, the implant is located in a gap between proximal and distal sections of the delivery guide member. The system may also be employed for implant delivery into solid organs or tissues including, but not limited to, skin, muscle, fat, brain, liver, kidneys, spleen, and benign and malignant tumors. Oftentimes, the implant is delivered to a target site in a blood vessel lumen.

In a general aspect, the system is a guidewire-less implant delivery system that includes a noninflatable, elongate delivery guide member having a proximal end and a distal end. The guide member is configured to direct at least one implant having an exterior and interior surface to an anatomical treatment site by manipulation by a user. The at least one implant has a delivery diameter prior to release of the at least one implant and is located proximally of the distal end of the delivery guide member prior to release. The at least one releasable joint is configured to maintain at least a section of the at least one implant at the delivery diameter until release of the at least one releasable joint. The guidewire-less system also has a flexibility and remote directability (e.g. torquability) such that a user may direct the distal end of the guide member into, and introduce, the at least one implant into a coronary artery solely by manipulation of the delivery guide member from its proximal end.

The present invention includes systems comprising any combination of the features described herein. Methodology described in association with the devices disclosed also forms part of the invention. Such methodology may include that associated with completing an angioplasty, bridging an aneurysm, deploying radially-expandable anchors for pacing leads or an embolic filter, or placement of a prosthesis within neurovasculature, an organ selected from the kidney and liver, within reproductive anatomy such as selected vasdeferens and fallopian tubes or other applications.

BRIEF DESCRIPTION OF THE DRAWINGS

Each of the figures diagrammatically illustrates aspects of the invention. Of these.

Figure 4:
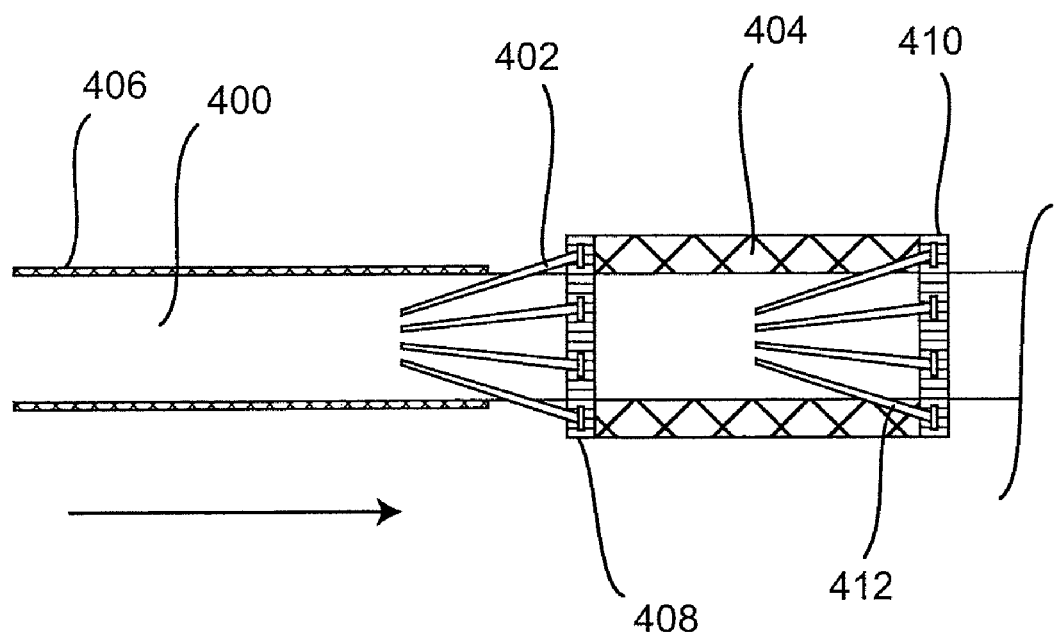
Figure 5A:
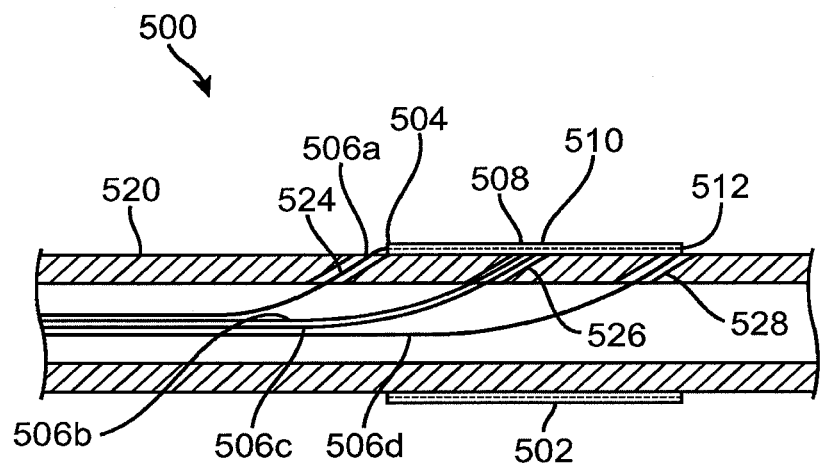
Figure 5B:
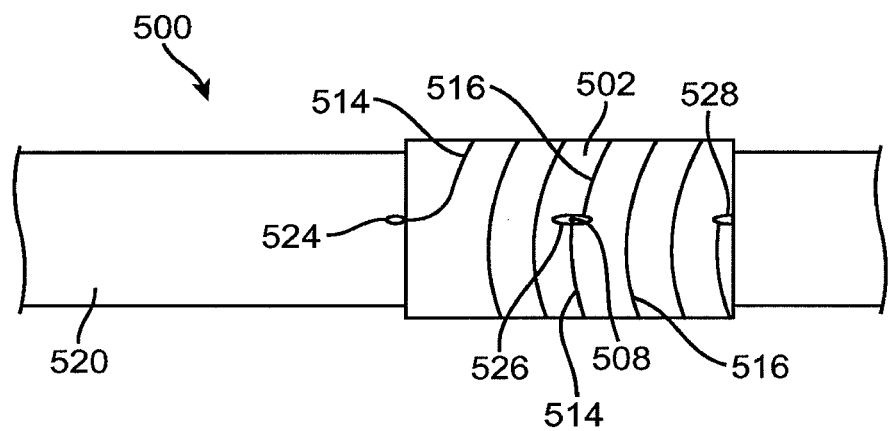
Figure 5C:
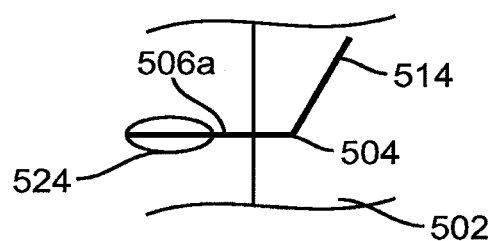
Figure 5D:
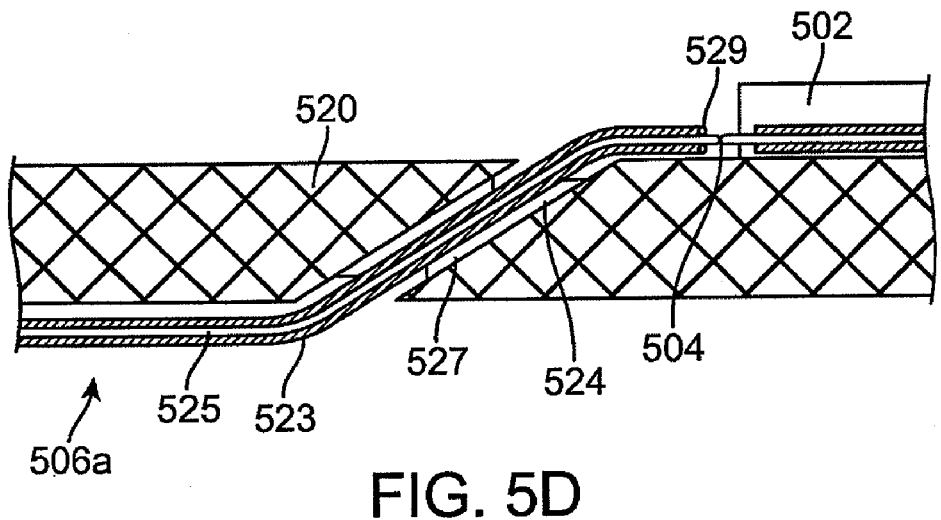
Figure 5E:
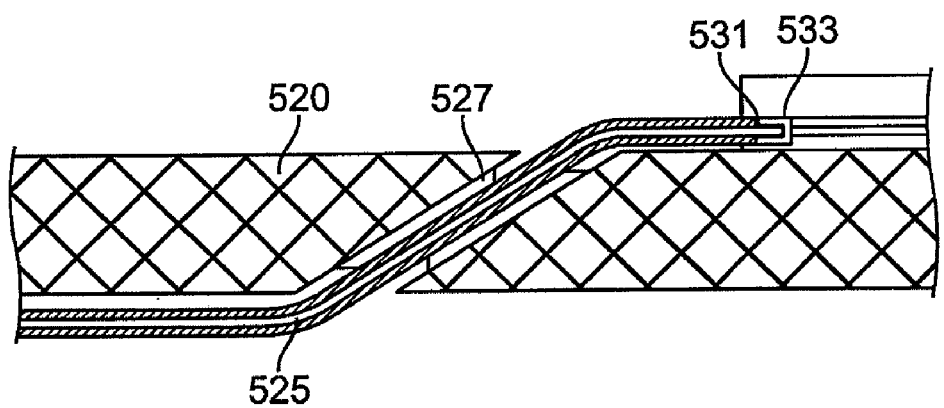
Figure 7:
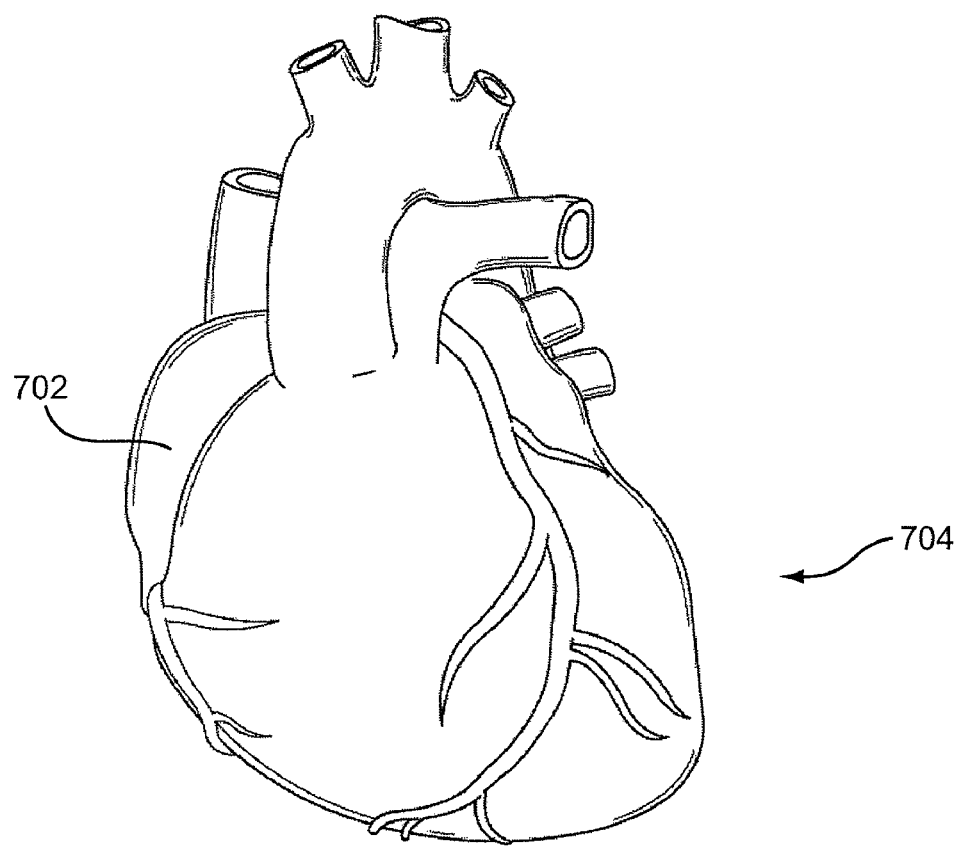
Figure 8:
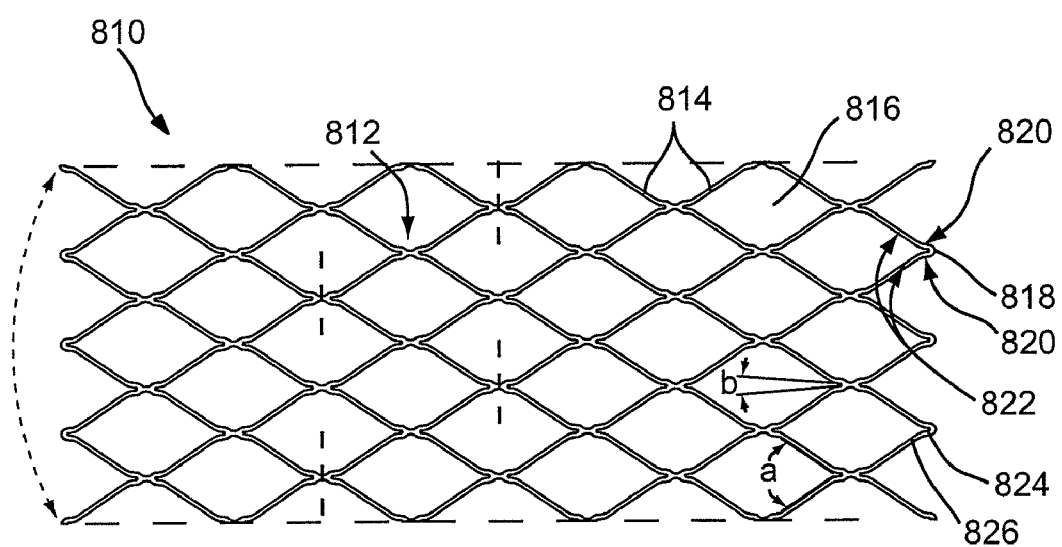
Figure 10:
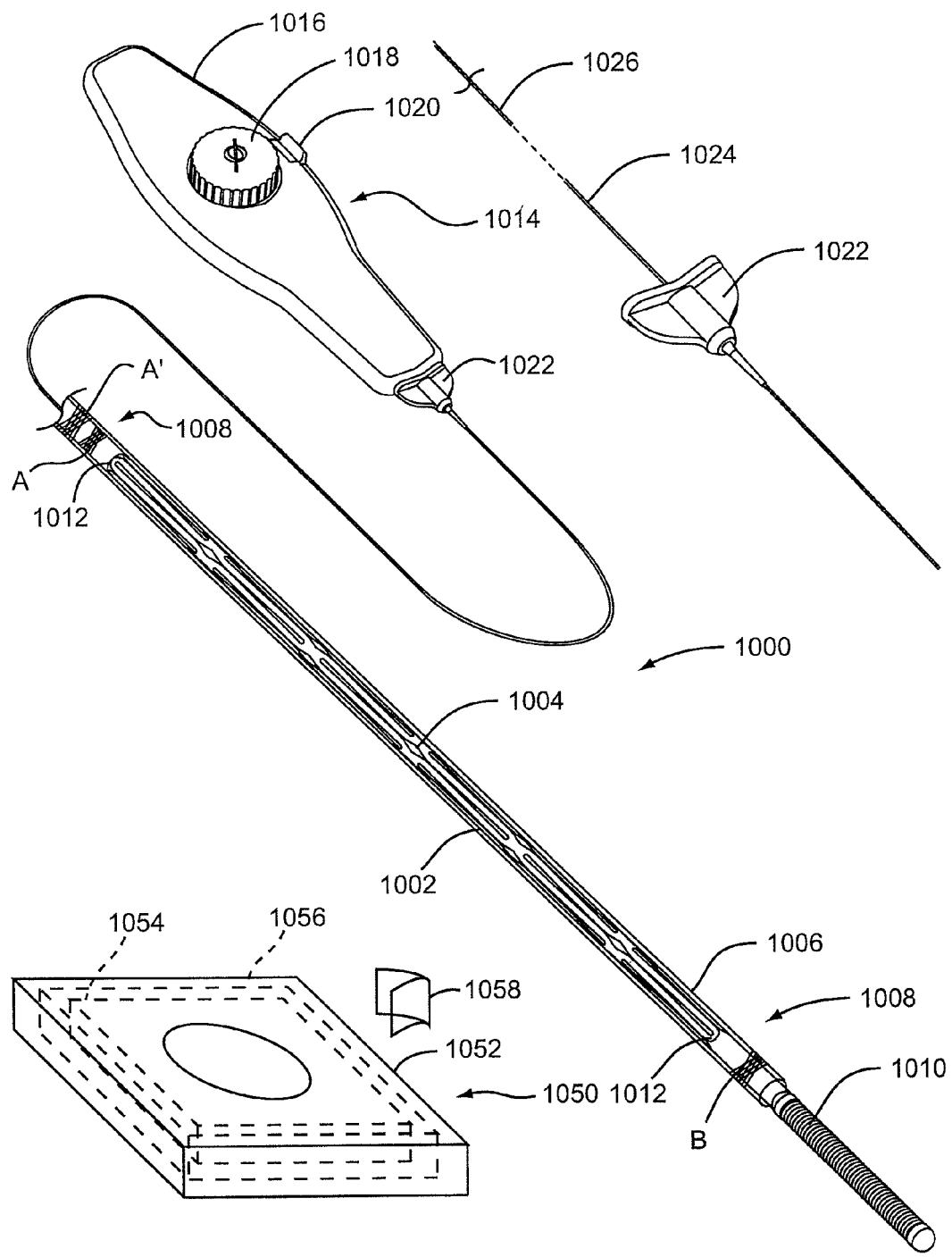
Figure 11A:
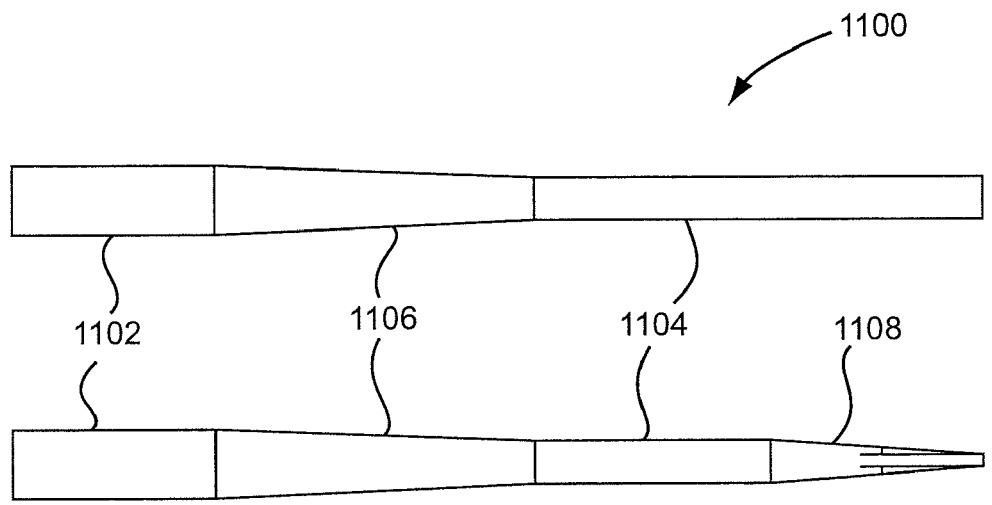
Figure 11B:
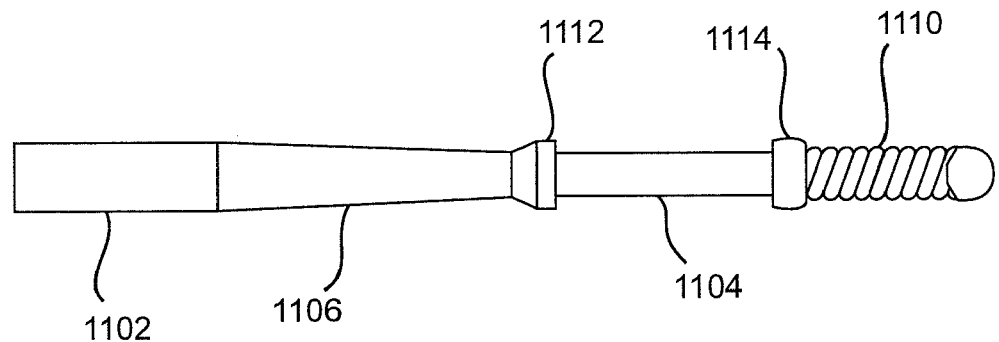
Figure 11C:
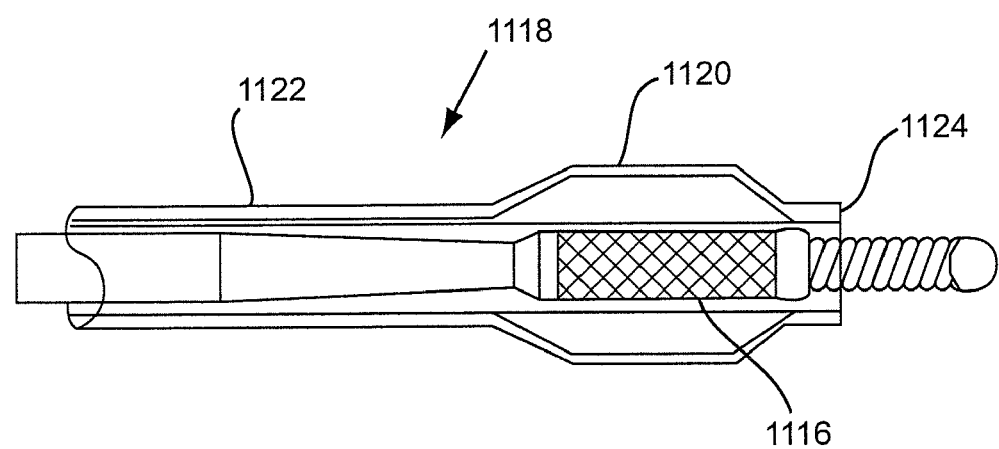
Figure 12A:
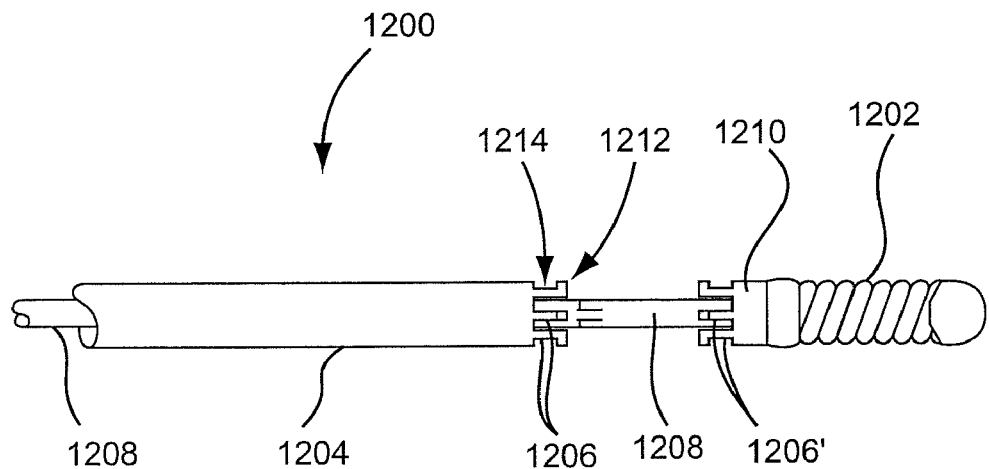
Figure 12B:
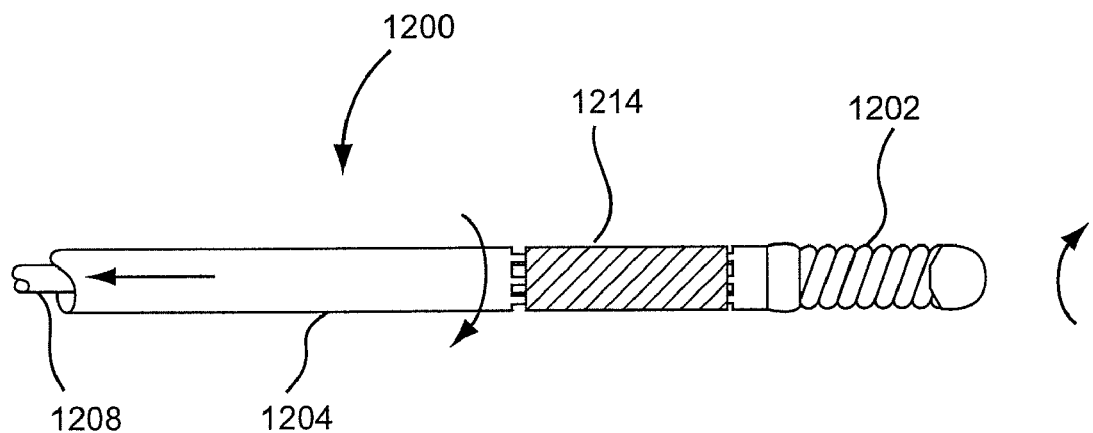
Figure 13A:
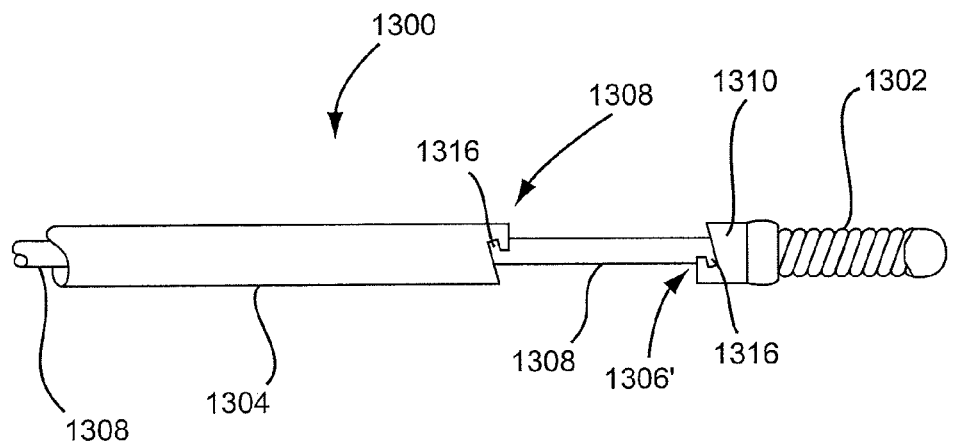
Figure 13B:
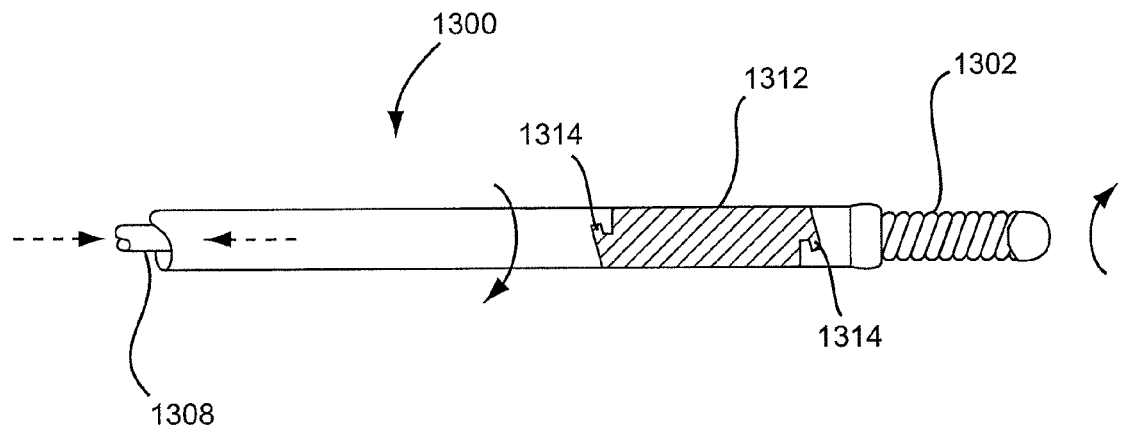

FIGS. $3C_1$ and $3C_2$ are longitudinal cross-sectional views of an implant delivery device having a mechanical release mechanism for deploying one end of an implant;

FIGS. $3D_1$-$3D_3$ are longitudinal cross-sectional views of an implant delivery device having a mechanical release mechanism for independently releasing the implant ends;

FIGS. $3E_1$-$3E_4$ are longitudinal cross-sectional views of an implant delivery device having a hydraulic release mechanism for independently releasing the implant ends;

FIGS. $3F_1$-$3F_2$ are longitudinal cross-sectional views of a variation of the hydraulic release mechanism described in $3E_1$-$3E_4$;

FIGS. $3G_1$-$3G_3$ are longitudinal cross-sectional views of an implant delivery device having a mechanical release mechanism according to another variation of the invention;

FIG. 4 is a longitudinal cross-sectional view of an implant delivery device having a mechanical release mechanism according to yet another variation of the invention;

FIGS. 5A-5C are longitudinal cross-sectional views of an implant delivery device having an electrolytic implant release mechanism;

FIG. 5D shows a longitudinal cross-sectional view of an implant delivery device having an electrolytic release mechanism according to another variation of the invention;

FIG. 5E shows a longitudinal cross-sectional view of an implant delivery device having a thermal release mechanism according to one variation of the invention;

FIGS. 6A-6D show the general method for serially releasing an implant at a target site;

FIG. 7 shows a heart in which its vessels may be the subject of one or more angioplasty and/or stenting procedures as described in connection with a more specific method of the invention;

FIG. 8 shows an expanded stent cut pattern as may be used in producing a stent for use in the present invention;

FIGS. 9A-9L illustrate stent deployment methodology to be carried out in connection with an stenting and/or angioplasty procedure;

FIG. 10 provides an overview of a system according to the present invention in connection with optional packaging;

FIGS. 11A-11C show side views of another variation of the invention, detailing constituent parts and distal end of a delivery system, respectively;

FIGS. 12A and 12B show side views of another implant delivery system, in unloaded and loaded configurations respectively;

FIGS. 13A and 13B show another type of delivery system in the same manner; and

Figure 14A:
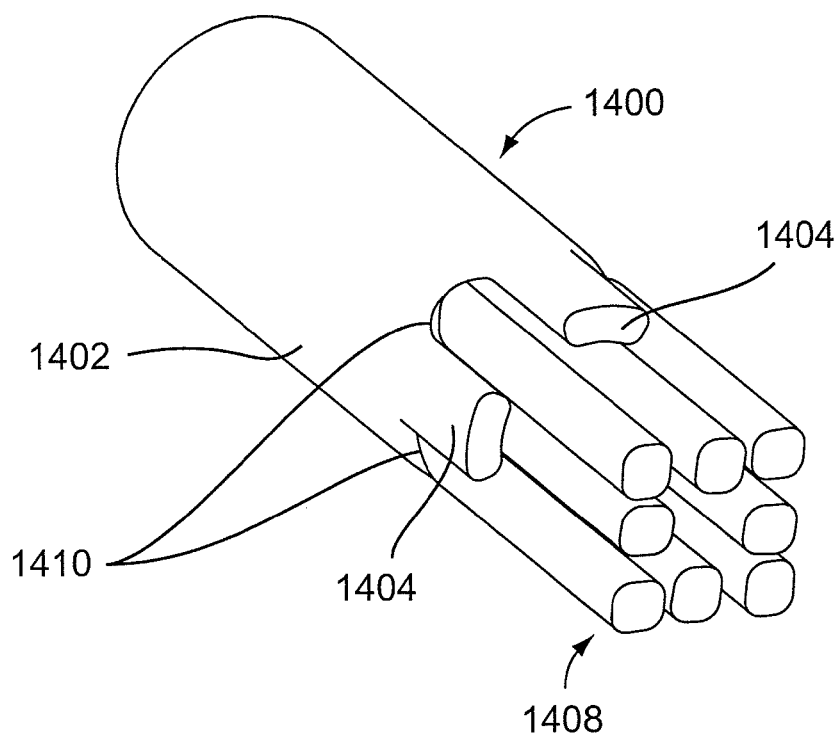
Figure 14B:
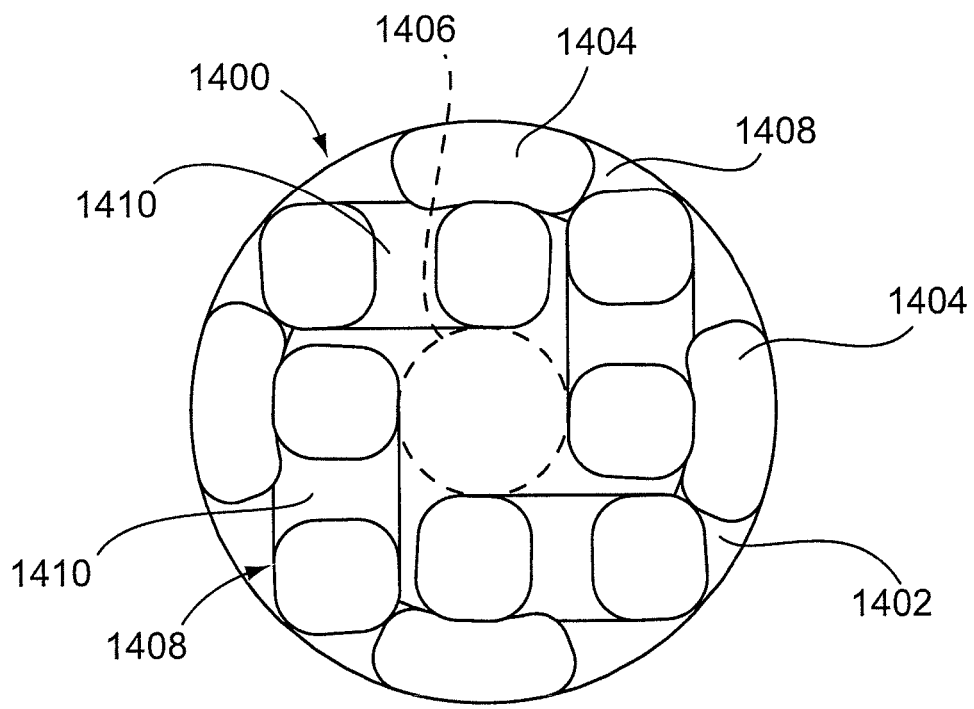

FIG. 14A is a partial sectional view of the end of a stent and corresponding delivery guide interface features; FIG. 14B is an end view of the members shown in FIG. 14A.

Variation of the invention from the embodiments pictured is, of course, contemplated.

DETAILED DESCRIPTION OF THE INVENTION

Described here are devices, systems, and methods for delivering implants into both open and solid regions of the body. The term "region" as used herein refers to luminal structures as well as solid organs and solid tissues of the body, whether in their diseased or nondiseased state. Examples of luminal structures include, but are not limited to, blood vessels, arteriovenous malformations, aneurysms, arteriovenous fistulas, cardiac chambers, ducts such as bile ducts and mammary ducts, fallopian tubes, ureters, large and small airways, and hollow organs, e.g., stomach, intestines, and bladder. Solid organs or tissues include, but are not limited to, skin, muscle, fat, brain, liver, kidneys, spleen, and benign and malignant tumors.

The device assembly generally includes an elongate, perhaps solid delivery guide, an implant, and one or more implant release mechanisms. Guidewire-less systems are used to deliver the one or more implants. By "guidewire-less" it is meant that the system does not require a guiding device of a diameter less than that of the system to reach a chosen implantation site. Instead, the guidewire-less system is flexible and remotely directable, the remote directability being such that a user may direct the distal end of the guide member into, and introduce (e.g. by torquing the member), the at least one implant into a coronary artery solely by manipulation of the delivery guide member from its proximal end.

Delivery Guide

The delivery guide is elongate and has a comparatively small effective diameter. It has the function of permitting delivery of the implant to a selected site and supporting the implant in a collapsed form during positioning and implantation. The delivery guide is usually noninflatable. It may also be solid, or may have a lumen extending therethrough, depending on such factors as the degree of flexibility required, type of associated release mechanism, the constituent material, and the like. The tip of the delivery guide may be tapered and/or straight, curved, or j-shaped, depending on factors such as physician preference, the anatomy of the tubular organ or region of interest, degree of stiffness required, and the like. The delivery guide may or may not include an outer spring coil, for, e.g., fluoroscopic visualization.

The delivery guide may be made from any biocompatible material including, but not limited to, stainless steel and any of its alloys; titanium alloys, e.g., nickel-titanium alloys; other shape memory alloys; tantalum; polymers, e.g., polyethylene and copolymers thereof, polyethylene terephthalate or copolymers thereof, nylon, silicone, polyurethanes, fluoropolymers, poly(vinylchloride), and combinations thereof. The diameter of the delivery guide may usually be about 0.013 cm to about 0.130 cm (about 0.005 inches to about 0.05 inches), more usually about 0.013 cm to about 0.076 cm (about 0.005 inches to about 0.03 inches), and more usually still about 0.015 cm to about 0.030 cm (about 0.006 inches to about 0.012 inches). In a preferred variation, the diameter of the delivery guide is approximately about 0.020 cm (about 0.008 inches).

A lubricious coating may be placed on the delivery guide if desired to facilitate advancement of the delivery guide. The lubricious coating typically will include hydrophilic polymers such as polyvinylpyrrolidone-based compositions, fluoropolymers such as tetrafluoroethylene, or silicones. In one variation, the lubricious coating may constitute a hydrophilic gel. Furthermore, the delivery guide may include one or more radioopaque markers that indicates the location of the distal section of the delivery guide upon radiographic imaging. Usually, the marker will be detected by fluoroscopy.

Implants

The implant itself may be of a shape tailored to achieve a specific purpose. As noted elsewhere, if the purpose of the implant is to provide or to maintain patency of an anatomical structure such as an artery or duct, the implant shape after implantation is itself tubular. The shape may be symmetric or asymmetric, as the purpose dictates.

Other shapes, including cage structures, may be used to provide patency to vessels or to act as collecting or coralling structures for occlusive members or materials.

If the purpose or task is to occlude a lumen or open region, the implant may have the form of an occlusive coil that remains helical or assumes a random orientation after deployment.

In one variation, the implant for placement into a luminal structure is a helical scaffold, e.g., a stent, but any scaffold shape that maintains patency of a lumen may be used. The stents are typically self-expanding stents, such as described in U.S. Pat. No. 4,768,507 to Fishell et al., U.S. Pat. No. 4,990,155 to Wilkoff et al., and U.S. Pat. No. 4,553,545 to Maass et al. In another variation, the implant is an occlusive member, e.g., an occlusive coil, such as described in U.S. Pat. No. 5,334,210 to Gianturco and U.S. Pat. No. 5,382,259 to Phelps et al.

The interior and exterior surfaces of the implant may be designed to prevent the activation of pathological processes during or after implant deployment. For example, in the case of a vascular stent, the exterior stent surface may be formed to be smooth to decrease the likelihood of intimal damage upon stent release (which would trigger the inflammatory process and attract atheromatous plaque-forming cells). The interior stent surface may also be smooth to minimize turbulent flow through the stent and decrease the risk of stent thrombosis.

Important physical properties of the implant to consider include, but are not limited to: length, (stent) diameter in the expanded state, degree of flexibility and lateral stiffness, and the like. These physical properties will be modified to account for such factors as lumen diameter, length of any stenosis, type of luminal structure, or solid organ or tissue involved.

Metals such as stainless steel and tantalum, or metal alloys such as alloys of nickel and titanium, specifically including superelastic alloys such as NITINOL or Elgiloy which are commonly used by those of skill in the art, may be used to form the implants. However, the implants may also be made from biodegradable polymers, e.g., copolymers of lactic and glycolic acid, or nonbiodegradable polymers, e.g., copolymers of ethylene and vinyl acetate.

The implants may also include a therapeutic agent. Examples of therapeutic agents that may be used in the implants include, but are not limited to, antibiotics, anticoagulants, antifungal agents, anti-inflammatory agents, antineoplastic agents, antithrombotic agents, endothelialization promoting agents, free radical scavengers, immunosuppressive agents, thrombolytic agents, and any combination thereof. If the implant is a stent, an antithrombotic agent is preferably included.

Examples of selective antithrombotic agents include acetylsalicylic acid, argatroban, cilostazol, copidogrel, cloricromen, dalteparin, daltroban, defibrotide, dipyridamole, enoxaparin, epoprostenol, indobufen, iloprost, integrelin, isbogrel, lamifiban, lamoparan, nadroparin, ozagrel, picotamide, plafibride, reviparin sodium, ridogrel, sulfinpyrazone, taprostene, ticlopidine, tinzaparin, tirofiban, triflusal, and any of their derivatives.

The therapeutic agent may be coated onto the implant, mixed with a biodegradable polymer or other suitable temporary carrier and then coated onto the implant, or, when the implant is made from a polymeric material, dispersed throughout the polymer.

The implant may include a radioactive material. The radioactive material may be selected on the basis of its use. For instance, the material may be included in an implant where the implant is in the form of a stent that is to be situated over a vascular stenosis. The radioactivity lowers the incidence of re-stenosis. Additionally, the radioactivity may serve the function of a tracer, to allow detection of the location of the implant during the procedure or anytime thereafter. Suitable radioactive tracers include isotopes of gallium, iodine, technetium, and thallium.

Release Mechanism

Figure 1A:
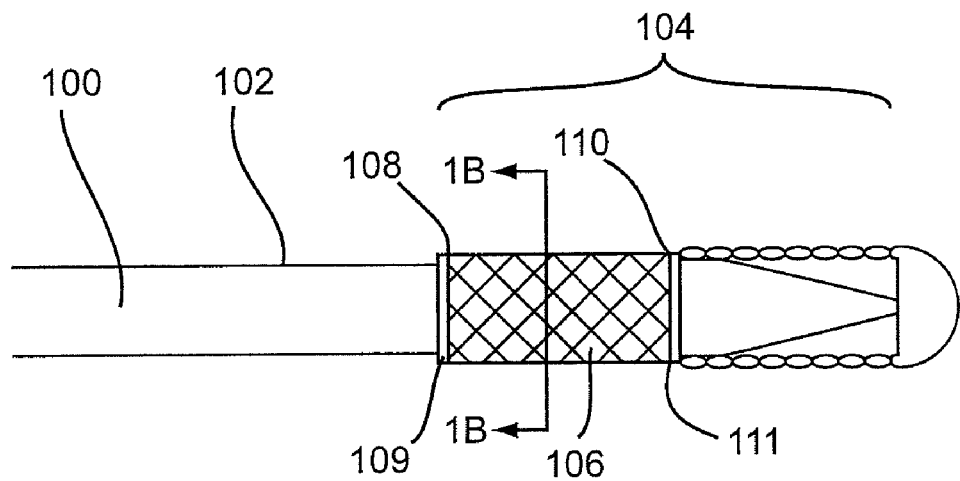
FIG. 1A is a side view of an implant delivery device with a partial cross-section of the distal section of the delivery guide.
Figure 1B:
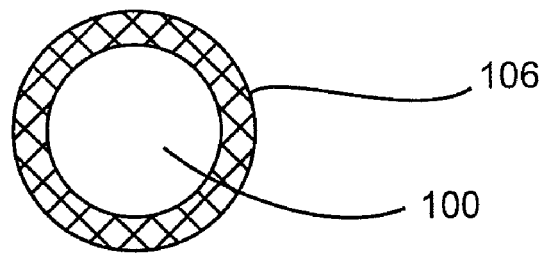
FIG. 1B is a cross-sectional view of the delivery guide and implant taken at line 1B-1B in FIG. 1A.

In one variation of the generic implant delivery system, as shown in FIG. 1A, the implant delivery system includes a delivery guide 100. Delivery guide 100 has a proximal section 102 and a distal section 104. An implant, in this case depicted as a stent 106, surrounds a portion of the distal section 104 of the delivery guide, and is releasably attached to the distal section 104 of the delivery guide. The implant 106, as shown in FIG. 1B, is concentrically adjacent to the delivery guide 100. Although the implant (106) is show as a stent in FIGS. 1A and 1B, depiction in this fashion is solely for the illustrative purpose of indicating the siting of the implant 106 on the delivery guide 100 with the distal and proximal implant release mechanism (109, 111). Various implant release mechanisms or structures are discussed in greater detail below.

Implant 106 is shown to be directly attached to, is contiguous to, the delivery guide 100 at the proximal end 108 of the implant and distal end 110 of the implant. In the system shown in FIG. 1A, implant 106 may be secured to the delivery guide 100 by such generic controllably releasable mechanisms as mechanical, thermal, hydraulic, and electrolytic mechanisms, or a combination thereof. Examples of these release mechanisms will be discussed below.

Consequently, release of the implant 106 from the delivery guide 100 may be achieved through a mechanical detachment process involving, e.g., twisting of the delivery guide, such as described by Amplatz in U.S. Pat. No. 6,468,301, or translational movement of the delivery guide in relation to the implant. Implant release may also be achieved using a thermally detachable joint, such as described in U.S. Pat. No. 5,108,407 to Geremia et al., an electrolytic detachable joint, such as described in U.S. Pat. No. 5,122,136 and U.S. Pat. No. 5,354,295, both to Gulglielmi et al., or a combination thereof.

Figure 2:
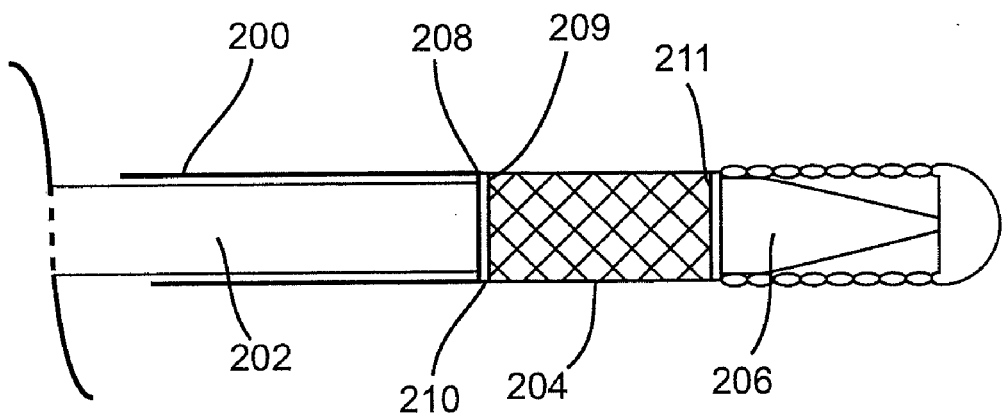
FIG. 2 is a side view of an implant delivery device having a tubular member (actuator) attached to the proximal implant end with a partial cross-section of the distal section of the delivery guide.

In another variation, and as shown in FIG. 2, the system includes a tubular member 200 co-axially mounted on a delivery guide 202. Tubular member 200 may form a component of the delivery guide 202 that cooperates with one or more of the releasable mentioned joints on the implant (209, 211) to release those joints (and therefore, release the implant 204) upon application of a releasing movement, axial or twisting. An implant, e.g., a stent 204, is mounted on a distal section 206 of the delivery guide and the distal end 208 of the tubular member is attached to the proximal end 210 of the stent. The distal end 212 of the stent is attached using a releasable joint 211 to the distal section 206 of the delivery guide 202.

Figure 3A:
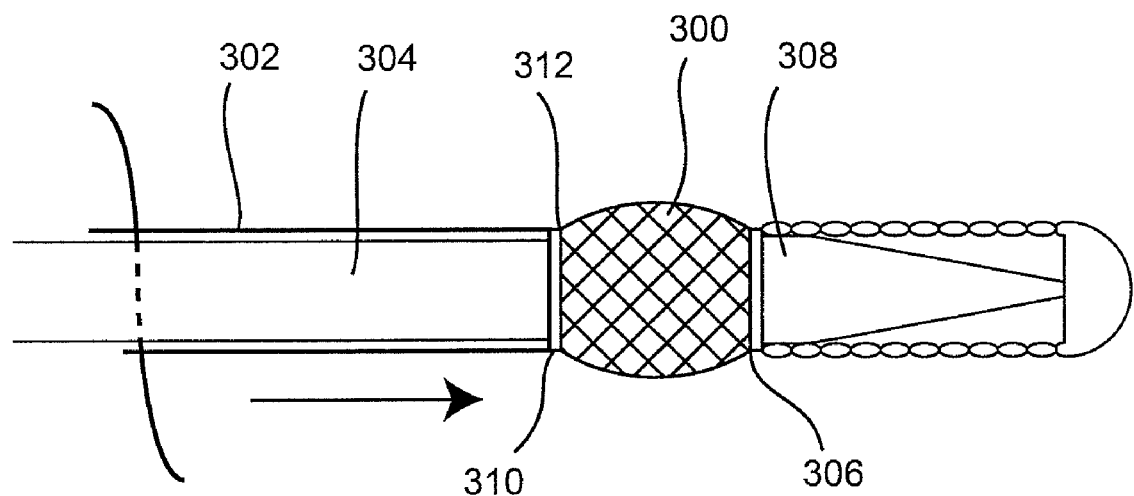
FIG. 3A is a side view of the implant in FIG. 2 being expanded by distally moving the tubular member towards the distal section of the delivery guide.

As mentioned above, tubular member mounted coaxially about the delivery guide may be used, that slides axially about that delivery guide, as a actuator to release the implant. The outer tubular member may also be used to pre-position the implant. For instance, prior to release, the outer tubular member may be used to expand the implant to therefore obscure its placement, and so to permit adjustment of the placement. FIG. 3A shows a stent 300 expanding as tubular member 302 is moved distally on the delivery guide 304, in the direction of the arrow. The stent is then released from the delivery guide. Specifically, the distal end 306 of the stent is released from a distal section 308 of the delivery guide, followed by release of the proximal end 310 of the stent from the distal end 312 of the tubular member. As mentioned above, the stent 300 may be secured to a distal section 308 of the delivery guide by such mechanisms as lock and key arrangements, biocompatible adhesives, soldering, or a combination thereof Consequently, stent release may be achieved through a mechanical detachment process, a thermal detachment process (e.g., by heat produced from an exothermic reaction), an electrolytic detachment process, or a combination thereof.

Figure 3B:
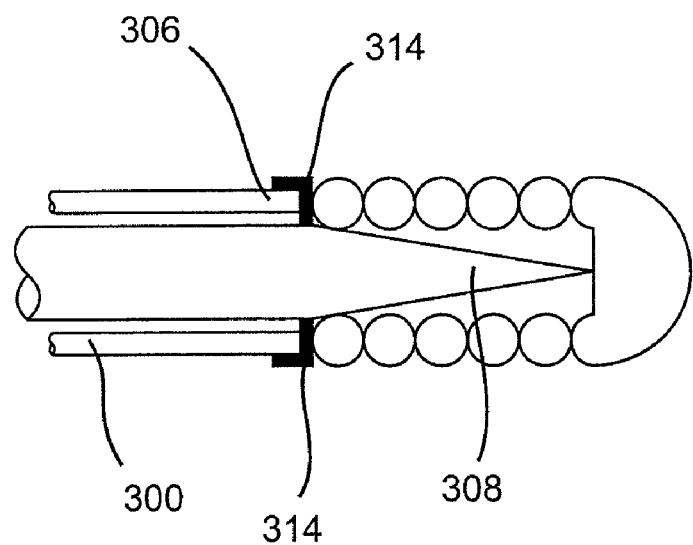
FIG. 3B is a longitudinal cross-sectional view of a distal implant release mechanism.

FIGS. 3B and 3C show yet another variation of a stent release mechanism. In FIG. 3B, brackets 314 may be used to couple the stent 300 to the distal section 308 of the delivery guide. Separation of the stent 306 from the brackets 314, e.g., by one of the detachment processes mentioned above, releases the distal end 306 of the stent from a distal section 308 of the delivery guide, allowing the stent distal end 306 to expand in the tubular organ.

Controllable release of an end of an implant from the delivery guide may be accomplished using the structure of FIG. 3C$_1$. Brackets 314 couple the stent proximal end 310 to the distal region 312 of the tubular member 313 that forms a portion of the delivery guide. The brackets 314 have a ramped region 316 which are proximally adjacent to an enlarged (and perhaps ball- or barrel-shaped) portion 318 of the delivery guide and bracket arms 320. The delivery guide and stent each have a delivery diameter, and these delivery diameters are substantially equal prior to release of the stent. When the actuator 305 is moved proximally, as shown by the direction of the arrow, the ball-shaped portion 318 forces the ramped regions 316 of the brackets outward from the delivery guide axis, in a radial fashion, causing the bracket arms 320 to be displaced radially outwardly from the proximal end 310 of the stent, thereby releasing the stent proximal end 310.

FIG. 3C$_2$ shows the results of moving the actuator 305 proximally. The clips (316) have rotated as shown due to the force exerted upon the ramps (317) by the ball (318). The implant (320) has expanded in diameter from that found in its undelivered form.

FIG. 3D$_1$, shows a delivery system 319 in which the two ends of the implant 321 may be independently deployed by using an actuator 304 having a proximal releasing ball 322 and a distal releasing ball 327. The implant 321 is located in a gap between sections of the delivery guide and are releasably attached to the delivery guide by brackets or clips. The two balls are spaced in such a way that, in the variation shown in FIG. $3D_1$, the distal ball 327 releases the distal end 331 of implant 321 and the proximal ball 322 then releases the proximal end 329 of implant 321 upon additional proximal movement of actuator 304. This sequence of events is shown in FIGS. $3D_1$, $3D_2$, and $3D_3$. The implant 321, is shown to be completely released in FIG. $3D_3$. In this variation, the implant 321 may be self-expanding, e.g., constructed of a superelastic alloy such as nitinol or another alloy having high elasticity, e.g., an appropriate stainless steel.

A structure similar to that shown in FIGS. $3D_1$, $3D_2$, and $3D_3$ may also be used to deploy an implant using fluid pressure as the releasing impetus.

FIGS. $3E_1$, $3E_2$, $3E_3$ and $3E_4$ show a hydraulic variation. Shown are the delivery guide 350, having a hollow lumen 352, a self-expanding implant 354 (shown variously as non-expanded (e.g., in a "first form") in FIG. $3E_1$, partially expanded in FIG. $3E_2$, and fully expanded in FIGS. $3E_3$ and $3E_4$ (e.g., in a "second form")), and an actuator 356 with a sealing member 358 and a radio-opaque member 360.

The implant 354 (here shown to be a stent or the like) is held to the delivery guide 350 during delivery to the selected treatment site using distal brackets 364 and proximal brackets 362 or clips or the like. The proximal and distal brackets (364, 362) either include regions that cooperate with the fluid in lumen 352 to move upon application of increased pressure in that lumen 352 and release the implant 350 or move in concert with a separate pressure sensitive motion component.

FIG. $3E_1$ shows the actuator 356 as the sealing member 358 approaches the various orifices or openings (proximal orifices 366 and distal orifices 368) communicating from the lumen 356 to the hydraulically or fluidly actuatable clips or retaining brackets (proximal brackets 362 and distal brackets 364).

Included in the description of this variation is a radio-opaque marker 360 on the actuator shaft 356 that allows the user to simply line up that actuator marker 360 with a corresponding radio-opaque marker 370 or the delivery guide 350, increase the pressure in lumen 352 (via syringe, pump, etc.) and deploy the proximal end 371 of implant 354. The interior pressure raises or rotates the proximal clips or brackets 362 and moves them out of contact with the implant 354. FIG. $3E_2$ shows the movement of the proximal end of implant 354 away from the delivery guide 350.

FIG. $3E_3$ shows the axial movement of actuator 356 distally to a position where the sealing member 358 is positioned to actuate distal clips or brackets 364 and release the distal end of implant. Again, a radio-opaque marker 374 (perhaps with an additional identification band 376) has been depicted to show alignment of the radio-opaque marker or band 360 on the actuator shaft 356 prior to the increase in pressure for deployment.

FIG. $3E_4$ shows final deployment at the implant 354 and proximal movement at the actuator 356, just prior to withdrawal of the delivery guide 350. The distal and proximal clips or brackets (362, 364) have relaxed to the surface of the delivery guide 350.

Alternatives to certain of the elements shown in the variation found in FIGS. $3E_1$ to $3E_4$ is seen in FIGS. $3F_1$ and $3F_2$ and includes, e.g., a cover element 380 to block or cover proximal orifices 366 during the pressurization of the distal orifices 368. The cover element 380 includes holes 382 to allow fluid flow past the cover element 380.

FIG. $3G_1$ shows a variation, of the described system in which an implant or stent 371 is maintained in position on a hollow delivery guide 373 using spring clips 375 proximally and 377 distally. The spring clips hold the implant 371 in place during delivery and against guide member 373. An actuator 379 is used to remove the clips 375, 377 sequentially and to release each end of implant 371 in an independent fashion. Clips. 375 and 377, after actuation or release, remain interior to the guide member 373 for later removal with that guide member. The system shown in FIGS. $3G_1$, $3G_2$ and $3G_3$ may be used to deliver a number of implants in a sequential fashion. Since the retainer clips 375, 377 remain within the guide member 373 after delivery, the actuator 379 is able to slide past the site on guide member 373 where the clips 375, 377 resided prior to implant 371 deployment, down to and distally to a site on the guide member having another implant for subsequent delivery. Consequently, an arrangement such as this may be used to deploy, in a sequential fashion, a number of stents or the like without withdrawal of the guide member.

In the variation shown in FIGS. $3G_1$, $3G_2$ and $3G_3$, the clips 375 and 377 are spring-biased to collapse within the lumen 381 of the guide member 373 once they are pushed into the respective slots 383 provided for such retraction. Such spring loaded clips retain the self expanding stent or implant 371 onto the face of guide member 373. Each of clips 375, 377 are shown in this variation to have hook members 387, 389 that engage the implant 371, often axially stretching the implant 371 and maintaining the delivery radius of the implant 371 as shown.

As shown in FIG. $3G_1$, actuator 379 is pushed distally along the outer surface of guide member 373 until it contacts the proximal end of clip 375. Further distal movement of actuator 379 urges clip 375 into lumen 381 thereby rotating horn 387 out of cooperating receptacle area in implant 371.

FIG. $3G_2$ shows the results of such movement after clip 375 has completed its springed closure within lumen 381. As shown in that Figure, the proximal end of implant 371 has expanded and yet the distal end of implant 371 remains closed and hooked to distal clip 377. This semi-open condition allows for some adjustment of the implant if needed. FIG. 3G3 shows the results of additional distal movement of actuator 379 until it contacts distal clip 377 (shown in FIG. 3G3 in its collapsed form) and thereby allowing the distal end of implant 371 to self-expand into the chosen treatment site.

FIG. $3G_3$ shows that guide member 379 is free. Implant 371 is shown in its self expanded form no longer adjacent the central guide member 379. Actuator 379 is situated within implant 371 and is no longer in contact with proximal clip 375 nor distal clip 377. Actuator 379 is thus able to continue distally to another implant containing site positioned in a more distal site on the guide member 373.

The mechanical variation shown in FIGS. $3G_1$, $3G_2$, $3G_3$ may be modified in such a way that the actuator is interior to the lumen of the guide member and deploys the implant upon distal movement of the actuator by providing an actuator with a slot or other "room-making" provisions or features in the actuator. The actuator and any retained clips would then be used to actuate the clips in the next more distal implant if so desired.

In yet a further variation, the system releases an implant (shown as a stent 404 in FIG. 4) attached to a delivery guide 400 by one or more attachment arms 402 positioned, e.g., at the implant proximal and distal ends, by sliding a tubular member 406, mounted co-axially on the delivery guide 400, distally over the delivery guide 400. The stent 404 is secured to the delivery guide 400 when the attachment arms 402 are in a radially expanded configuration (as illustrated in FIG. 4). The tubular member 406 urges the attachment arms 402 into a compressed configuration as it slides distally over the delivery guide 400, in the direction of the arrow. When the attachment arms 402 are compressed by the tubular member 406, they are moved inward from the stent 404, toward the central axis of the delivery guide 400, thereby releasing the stent 404 from the delivery guide 400. Stent detachment occurs in a serial fashion as the tubular member 406 is moved distally, with detachment of the stent proximal end 408 occurring before detachment at the stent distal end 410. Consequently, if the stent position requires readjustment after detachment of the stent proximal end, the stent may be repositioned prior to detaching the stent distal end. In one variation, the tubular member is a balloon catheter.

The attachment arms 402 are generally made from the same materials as the delivery guide 400, e.g., stainless steel or nickel-titanium alloy, and will typically have a length, thickness, shape, and flexibility appropriate for its intended mechanism of release. The distal ends 412 of the attachment arms may be of any design, so long as one or more of them, when in a radially expanded configuration, secures a portion of a stent to a delivery guide, and when in a compressed configuration, releases that same stent portion from the delivery guide.

The tubular member may be a thin-walled tube (e.g., approximately 0.005 cm (0.002 inches) in thickness) with an outside diameter ranging from about 0.025 cm to about 0.139 cm (0.010 inches to about 0.055 inches), more usually from about 0.025 cm to about 0.05 cm (0.010 inches to about 0.020 inches), and more usually still from about 0.025 cm to about 0.035 cm (0.010 inches to about 0.014 inches). Depending on such factors as degree of flexibility or durometer required, they may be made from various metals or metal alloys, including, but not limited to, stainless steel and nickel-titanium alloy, or from various polymers, such as polyvinyl chloride, polyethylene, polyethylene terephthalate, and polyurethane.

FIGS. 5A, 5B, and 5C show a variation of the described delivery system 500 in which a member of electrolytic delivery joints are used to deploy an implant 502, such as a stent.

The electrolytic delivery joints shown here (e.g., 504 in FIG. 5C) are well known as controllable delivery joints for placement of vaso-occlusive coils. One such commercially available device using an electrolytically detachable joint is sold by Target Therapeutics, a subsidiary of Boston Scientific Corp., as the Guglielmi Detachable Coil (or "GDC"). Numerous patents to Dr. Guglielmi describe the theory of its use.

In essence, the electrolytically erodible joint is a section of an electrical circuit that is not insulated and is of a metallic material that does not form insulating oxides when exposed to an aqueous environment (e.g., aluminum and tantalum) and is sufficiently "non-noble" that is will either electrolytically erode by ionic dissolution into an anatomical fluid or, perhaps, electrochemically erode by forming readily soluble oxides or salts.

The erodible joint 504 shown in FIG. 5C is a bare metal of a size, diameter, etc. that erodes away when a current is applied to insulated wire 506. The current flow is from a power supply through insulated wire 506, bare joint 504, into the ionic anatomical fluid surrounding the site to be treated, and back to a return electrode situated perhaps on the patient's skin and then back to the power supply. The current flows through the circuit so long as the joint 504 exists.

With that background, FIG. 5A shows a device having several joints (504, 508, 510, 512) that each may be independently severed to controllably deploy the implant 502. Implant 502 is shown having coils (514, 516) (FIG. 5B) that are terminated at each end by an erodible joint and that, prior to the severing of a joint, hold this implant 502 to the surface of the delivery member 520. The implant 502 is self-expanding, once released. The wires forming the two coils in this variation slide within the implant or "uncoil" and thereby allow the implant body itself to expand. The coils may comprise (if electrically connected to the erodible joint) a metal that is higher in the Mendelev Electromotive Series than is the composition at the electrolytic joint or the coils may comprise a polymer that may be bio-erodible or not.

In any case, a suitable way to assure that the coils (514, 516) maintain the low profile of the implant 502 during delivery is via the placement of the various conductive wires or elements (506a, 506b, 506c, 506d) through the adjacent holes (524, 526, 528) and fill the holes with e.g., an epoxy to hold all in place. Independently causing current to flow through each of the joints will release the implant in the region of the released joint. Once all joints are eroded, the implant is released.

Although release from proximal and distal ends of the tubular form of the implants has been described, detachment from a delivery guide is not so limited. In another variation, the stent is attached to the delivery guide at one or more positions along the length of the stent, in addition to attachment at the proximal and distal implant ends. Once the distal stent end is released, the additional attachments may be independently released until detachment at the proximal implant end releases the implant entirely from the delivery guide. Serial release may provide better control of positioning in tubular organs.

FIGS. 5D and 5E show in more detail, the components of an electrolytic joint (as may be found in FIGS. 5A, 5B and 5C) and another electrically actuated joint using a meltable or softenable or polymerically sizable joint.

FIG. 5D shows the insulated wire 506a with insulation 523 and conductor 525. The electrolytic joint 504 is also shown. In this variation, the wire 506a is shown to be secured into hole 524 in the delivery guide wall 520 by, e.g., an epoxy 527, an alternative or cooperative band or component 529 holding the wire 506a to the surface of guide member 520 is also shown. After erodable joint 504 is eroded, the implant of 502 expands and leaves the securement band 529 on the delivery guide 520.

FIG. 5E shows a similar variation but the joint comprises a thermoplastic adhesive or shape changing polymer 531 situated on the end of wire 525 and within a cup or other receptacle 533. The adhesive is of the type that changes form or viscosity upon application of current to the joint. In this variation, the thermoplastic is rendered conductive, but resistive, by introduction of material such as carbon black into the polymeric adhesive. As soon as the polymer changes its shape, form, or phase, the implant expands to the desired form about the central guide member 520 again, the wire may be held in place with an adhesive 527 if so desired.

Although the figures show wires and other remnants of the joints remaining exterior to the central guide member 520 and the others shown and described here, it is desirable that these not be situated in such a way that they will harm the tissues into which they are placed.

Another variation of the invention is shown in FIG. 10. Note that this variation of the invention (or any of the others described herein) is optionally set in the packaging as also shown in FIG. 10 and described in further detail below.

In any case, FIG. 10 portrays a delivery guide member 1000 with a stent 1002 held in a collapsed configuration upon a core wire 1004. A sheath 1006 is provided over and around the stent. A "core wire" as used herein generally comprises a common metallic member. However, the wire may be coated or covered by a polymeric material (e.g., with a lubricious material such as TEFLON®) or otherwise. Still further, the "wire" may be a hybrid structure comprised of a metal and a polymeric material (e.g. Vectra™, Spectra™, Nylon, etc.) or composite material (e.g., carbon fiber in a polymer matrix). The wire may be a filament, bundle of filaments, cable, ribbon or in some other form; however, it is generally not hollow.

The portion of sheath 106 restraining the stent may fully surround the stent or only subtend a partial circumference of the stent, it may be split, splittable, comprise a plurality of member or may otherwise be provided around the stent to hold or restrain it in a collapsed profile. Oftentimes, the sheath (especially when provided as a tubular member) will be polymeric material, such as polyamide or PET. However, the sheath may comprise hypotube. "Hypotube" or "hypotubing" as referred to herein means small diameter tubing in the size range discussed below, generally having a thin wall. The hypotube may specifically be hypodermic needle tubing. Alternatively, it may be wound or braided cable tubing, such as provided by Asahi Intec Co., Ltd or otherwise. As with the "wire" discussed above, the material defining the hypotube may be metallic, polymeric or a hybrid of metallic and polymeric or composite material.

To accommodate stent 1002, the core member/wire may be stepped down in size to form a recessed stent receiving area 1008 as shown. Such a configuration is generally desired in that (at least at the distal end), the sheath restraining the stent can be straight-gauge or constant diameter material. However, alternative configurations are contemplated.

Delivery guide 1000 will typically have an atraumatic tip 1010. This feature, together with having the stent ride or be set over an integral core wire (thereby stabilizing the same and offering the potential to capture the stent at both ends with stop sections 1012 or along at least a portion of its length by an underlying core member pattern complimentary to the stent pattern, etc.), distinguishes this embodiment of the present invention structurally and functionally from a basic sheath and pusher type system or one that rides over a discrete guidewire. In addition, the latter type of systems can not be made as small as this embodiment of the present invention (for reason of at least the clearance requirements for the guidewire lumen).

By providing a minimalistic system in which there is only a core wire including a distal atraumatic tip and a sheath to restraint the stent, a highly cost and space-efficient delivery solution is provided. Stated otherwise, the delivery guide substantially consists of a core member or wire, having an atraumatic tip and a sheath (at least at the distal end). Yet another way of describing this embodiment of the invention is to say that it has no movable member intermediate to the sheath and core member. Yet, it includes a highly desirably and efficacious atraumatic tip.

From any perspective, in this system, the core member and any stop or other stent-holding features are fixed such that relative movement between them is not possible. Accordingly, when sheath 106 is withdrawn, the stent is unable to move proximally and, thus, expands as the sheath is removed from its body.

As for the atraumatic tip required of the variation of the invention shown in FIG. 10 (or possibly used in other variations of the invention), it may comprise a plurality of spring coils (as shown) attached to a tapered wire section. At a distal end the coils typically terminate with a bulb or ball that is often made of solder. In such a construction, the coils and/or solder are often platinum alloy or another radiopaque material. Of course, the wire section to which the coils are attached may be tapered, but need not be tapered. In addition, alternate constructions for the atraumatic tip are possible. For instance, molding or dip-coating with a polymer may be employed. In one example, the atraumatic tip may comprise a molded tantalum-loaded 35 durometer Pebax™ tip. However constructed, the atraumatic tip may be straight or curved; the latter configuration possibly assisting in directing or steering the delivery guide to a desired intravascular site or other treatment location.

While many of the other variations of the invention may not require an atraumatic tip (even though it is often highly advantageous), such a structure is required of the delivery guide 1000. On the other end of the delivery device, a custom handle 1014 is preferably provided.

Handle 1014 is adapted for rotating actuation by holding body 1016, and turning wheel 1018. This might be a one-handed or a two-handed operation. Naturally, other handle designs are contemplated. A full range of reciprocal actuators including sliders, or other rotating means such as rollers operating in either axis normal to that shown may be employed. In addition, other form-factors for the handle may be adopted. Examples include pen-like and puck-like shapes. Generally, less bulky system will be preferred to facilitate handing and minimize delivery system dislodgement or position loss in the case of dropping the same.

However, configured, the handle may include a lock 1020 as shown. In addition, the handle system shown includes a removable interface member 1022 to facilitate removal of the handle from a proximal length 1024 of the delivery system. In which case, the interface piece will be lockable with respect to the body and preferably includes internal features for disengaging the handle from the delivery guide. Once accomplished, it will be possible to attach or "doc" a secondary length of wire 1026 on the delivery system's proximal end, allowing the combination to serve as an "exchange length" guidewire, thereby facilitating changing-out the balloon catheter or performing another procedure. Alternatively, the wire may be an exchange-length wire.

Packaging 1050 for any of the delivery systems (1000, etc.) may include one or more of an outer box 1052 and one or more inner trays 1054, 1056 with peel-away coverings as is customary in packaging of disposable products provided for operating room use. Naturally, instructions for use can be provided therein. Such instructions may be printed product 1058 or be provided in connection with another readable (including computer-readable) medium. The instructions may include provision for basic operation of the subject devices and/or methodology.

As for the delivery systems in FIGS. 11A-11C, it offers some similarity to the sheath-based delivery system of FIG. 10. The primary difference is that in this case, the "sheath" holding the stent in a collapsed configuration is, in fact, a balloon catheter. The construction of the devices, may otherwise be identical.

In this regard, FIG. 11A shows the distal end of a core wire 1100 and 1100'. Both wires are shown tapering in sections 1106 from a larger diameter proximal section 1102 to a smaller stent-carrying section 1104. Wire 1100' includes yet another taper 1108 to accommodate a coil tip 1110 as shown in FIG. 11B. Depending on the size of the device, were no taper 1108 is provided, it may be desired to decrease the overall thickness of the stent carrying section and portions distal thereto in order to achieved sufficient flexibility.

Proximal to the stent carrying section 1104 is a stop 1112 or blocker. As shown, this member is affixed or connected to the core wire. Yet, it could be provided integrally therewith such as by grinding the feature in the core member (e.g., by decreasing the taper of section 1106). A distal stent stop 1114 is shown provided in connection with atraumatic coil tip 1110.

In FIG. 11C, the assembly of FIG. 11B is brought together with a stent 1116 held in a collapsed configuration by balloon catheter 1118 carrying at least one balloon. The balloon 1120 of the catheter is shown inflated. However, during delivery, that will obviously not be the case. Depending on the configuration of the device, the balloon might be the primary balloon for effecting predilatation. In the alternative, it may simply be used for postdilatation of an emplaced stent.

In any case, stent release will typically be effected by withdrawing the catheter body 1122 until a distal end 1224 of catheter 1118 clears the stent. With such a system, stent release may be accomplished in the smallest of vessels. By incorporating the balloon into the restraint for the stent, the system enables one to forgo the use of separate balloon catheter and stent delivery systems. At minimum, this consolidation can reduce the number of steps required to complete a procedure (thus reducing operating time).

Yet another class of delivery guides is shown in FIGS. 12A-14B. In each of a number of different ways, these delivery systems hold a radially-expandable prosthesis (such as a stent) in a collapsed configuration for delivery without the use of a restraint or active (hinging, deforming, electrolyticlly corroding, etc.) latching or locking members as in the other variations of the invention.

FIGS. 12A and 12B show of first of these devices. As with the other variations of the invention above, delivery guide 1200 preferably includes an atraumatic tip 1202. A body or shaft 1204 of the device in the form of a tube or sleeve includes hooks 1206 at a distal end. The body is advantageously made of hypotubing in order to manufacture the hooks integral thereto.

Complementary hooks 1206' are formed distal thereto and supported by core member 1208. Hooks 1206' may be formed in connection with a ring 1210 or be provided otherwise. In any case, the hooks (numbering at least two per side to balance forces) are dimensioned with a prong 1212 and recess 1214 suited for receipt of a stent. Together a complementary set of hooks 1206/1206' receive a stent and stretch it to hold it in a collapsed form when stretched or extended axially as shown in FIG. 12B. Additionally, or alternatively, a twisting mode of stent compression or retention may be employed.

Regardless, in the configuration shown where the hooks have no overhang (so as to facilitate stent release) the system relies on friction between the stent and hooks to hold the stent in place when the stent is axially stretched. Still, interference features between the stent and hooks may be provided to facilitate hold-down. Whatever the case, stent release is accomplished by releasing the tension and/or torque holding the stent in its collapsed profile.

While the system of FIGS. 12A and 12B is suited for use in holding a stent in simple tension, by twisting alone, or by a combination of these modes, the variation of the invention shown in FIGS. 13A and 13B is specifically adapted for incorporation of at least some twisting to hold down the stent. In this variation of the invention, a delivery guide 1300, again, preferably includes an atraumatic tip 1302. Furthermore, a body or shaft 1304 (advantageously, hypotubing) and a core wire member 1308 are provided. However, in the variation shown in FIGS. 13A and 13B, rather than providing radially-oriented hooks radially oriented thread-like graspers 1306 and 1306'. At a proximal side of the device, they are shown integral with the hypotube. At a distal end, they are shown fabricated in connection with a ring 1310.

As shown in FIG. 13B, the graspers (ranging in number from at least one per side to very many—acting like teeth) capture a complimentarily shaped stent 1312 having keys 1314 sized to fit within grasper slots 1316. As mentioned above, a stent is collapsed or at least held in collapsed state for delivery by imparting a torque to the system. In addition, the stent may be placed under tension as indicated—pushing the core wire forward relative to the hypotube (or vice versa). Naturally, release will be effected upon removal of the wind-up and/or pull-down forces. In which case, the stent will be able to expand and free its keys 1314 from slots 1314 by way of radial expansion.

A final mode of twist-based stent hold down is illustrated in connection with FIGS. 14A and 14B. FIG. 14B shows a chuck-type 1400 feature having a body 1402 and a plurality of extensions 1404 therefrom. The body may be provided by hypotubing or a separate member. In any case, the device is preferably configured to ride over a core wire 1406 of a delivery as with the hook or gasper features in the preceding variations of the invention.

The number of extension will depend on the stent 1408 with which the chuck is designed to interface. As shown in FIG. 14B, a four-extension chuck interfaces neatly with a stent including four strut ends 1410. When closely-packed as shown, counter rotation of complementary pairs of chucks 1400 will capture the stent. Thus captured, the stent may be held down to a core member for delivery by this mode alone. In the alternative, some measure of tension may be applied thereto. Whatever the hold-down mode desired, it can be appreciated that the system of FIGS. 14A and 14B represents a sort of "self-locking" system.

What is more, the retention system is very compact and can be made quite robust as shown in the to scale drawings provided of the same. In order that the stent pack so cleanly as shown when twisted, it may be desired to pre-curve its shape. That is to say, the stent may be configured so that when it is twisted that its members go from a pre-twisted shape to a straightened configuration as shown. The amount of shaping to account for hold-down twist, may be in the form of a simple bias or helix, S-curves or other shape(s). The particular configuration of the stent or degree of pre-twist/pre-curve as will be effective in facilitating the most efficient implant packing may be determined through iterative design or by modeling techniques that are well know in the art. Naturally, these pre-shaping principles to account for or accommodate the twisting of the stent as discussed with respect to the variation of the invention shown in FIGS. 14A and 14B may be applied to the other variation of the invention employing a torque or twist to the implant in holding the same in preparation of an for delivery.

Delivery Method

The implant delivery devices described herewith may include multiple implants on a single delivery guide or may be used in conjunction with other instruments, as seen appropriate, to treat the target site. In general, the tubular organ of interest is percutaneously accessed, but the method of accessing will usually be dependent on the anatomy of the organ, medical condition being treated, health status of the subject, and the like. Consequently, access by a laparoscopic or open procedure may also be obtained.

Figure 6A:
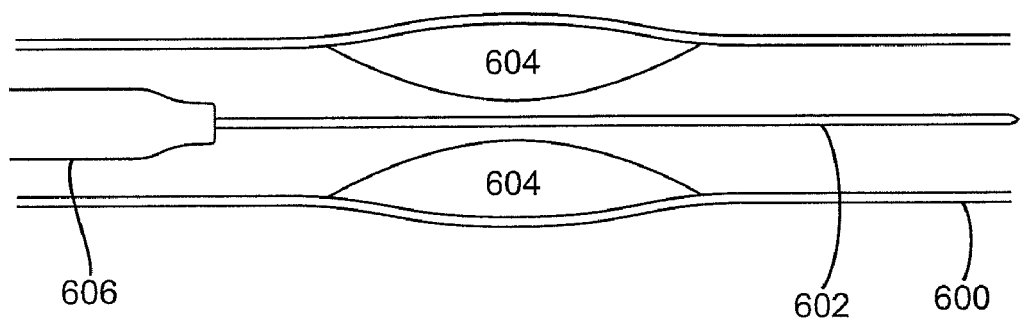
Figure 6B:
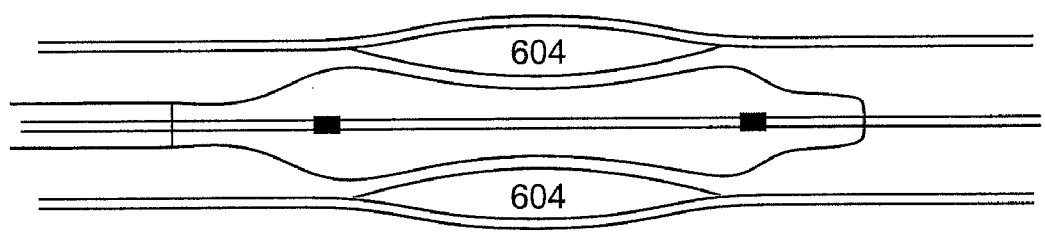
Figure 6C:
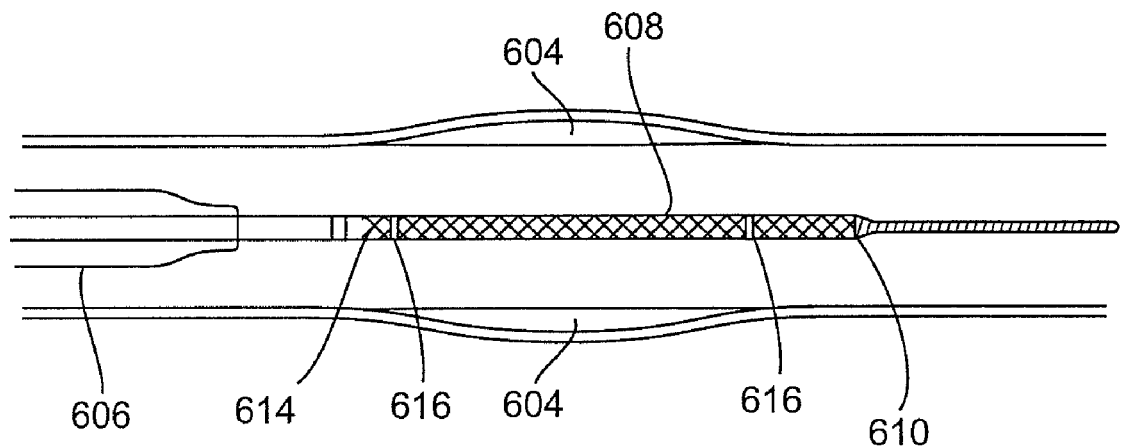
Figure 6D:
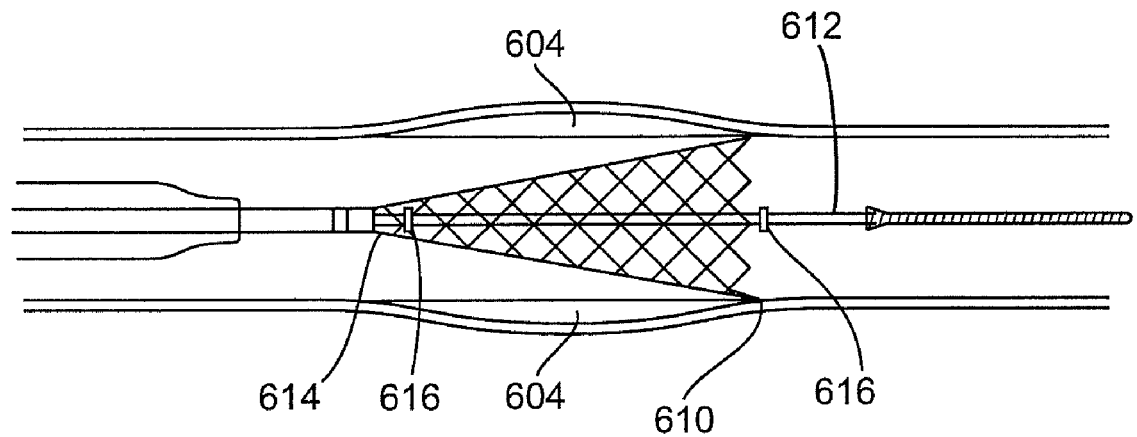

FIGS. 6A-6D show the general method of deploying a stent using my described system. After obtaining access to the tubular organ of interest 600 (blood vessel in FIG. 6A), a delivery guide 602 is placed through the selected area of stenosis 604 at the target site. A balloon catheter 606 is then advanced over the delivery guide 602, and balloon angioplasty performed to dilate the area of stenosis 604 (FIG. 6B). The balloon catheter 606 is then retracted proximally and the delivery guide 602 exchanged for a stent delivery device 608 (FIG. 6C). Appropriate placement of the stent is guided by radioopaque markers 616 on the delivery guide 612. The distal end 610 of the stent is then released from the delivery guide 612. At this point, stent position may again be checked by verifying the location of the radioopaque markers. The proximal stent end 614 is then released from the delivery guide 612.

If desired, an embolic filter may be used during stent deployment to filter any debris generated during the procedure. The filter will usually be attached to the delivery guide such that it filters debris distal to the stent, but may also be attached to the delivery guide proximal to the stent, or both distal and proximal to the stent. The filter may be of any design, as long as it does not affect the substantially atraumatic, low profile, and controlled release characteristics of the stent delivery device. Typically, the filter is basket-shaped, and made from a shape-memory material, e.g., an alloy of titanium and nickel. The filter will usually be contained within the balloon catheter lumen, and deployed to its pre-designed shape once the balloon catheter is removed. Following placement of the stent, the balloon catheter may be advanced over the delivery guide to enclose the filter with any accumulated debris. The balloon catheter, filter, and delivery guide may then be removed from the body.

Turning now to FIG. 7 a heart 702 is shown in which its vessels may be the subject of one or more angioplasty and/or stenting procedures in more specific methodology according to the present invention. To date, however, significant difficulty or impossibility is confronted in reaching smaller coronary arteries 704. If a stent and a delivery system could be provided for accessing such small vessels and other difficult anatomy, an additional 20 to 25% percutaneous coronary procedures could be performed with such a system. Such a potential offers opportunity for huge gains in human healthcare and a concomitant market opportunity in the realm of roughly 1 billion U.S. dollars—with the farther benefit of avoiding loss of income and productivity of those treated.

Features of the present invention are uniquely suited for a system able to reach small vessels (though use of the subject systems is not limited to such a setting.) By "small" coronary vessels, it is meant vessels having a inside diameter between about 1.5 or 2 and about 3 mm in diameter. These vessels include, but are not limited to, the Posterior Descending Artery (PDA), Obtuse Marginal (OM) and small diagonals. Conditions such as diffuse stenosis and diabetes produce conditions that represent other access and delivery challenges which can be addressed with a delivery system according to the present invention. Other extended treatment areas addressable with the subject systems include vessel bifurcations, chronic total occlusions (CTOs), and prevention procedures (such as in stenting vulnerable plaque).

Assuming a means of delivering one or more appropriately-sized stents, it may be preferred to use a drug eluting stent in such an application to aid in preventing restenosis. However, bare-metal stents may be employed in the present invention. The present invention is advantageously employed with self-expanding stents. However, the teachings herein may be adapted for application in the context of balloon-expandable stents.

In any case, features of the present invention are provided in order to hold a prosthesis or implant (e.g., a stent) to be delivered in an access or deployment configuration, after which, the implant assumes its deployed or expanded configuration. Hold-down features may restrain a stent under compressive forces, whereupon release, the stent "springs" open. Alternatively, the stent (or other implant) may simply be secured to the delivery member, where some other mechanism is used to open the stent (e.g., ceasing a flow of chilled saline, thereby allowing a shape memory devices (e.g., NiTi) to warm in order that a material phase change from martinsite to austenite will cause the stent to open).

While some might argue that the particular role and optimal usage of self expanding stents has yet to be defined, they offer an inherent advantage over balloon expandable stents. The latter type of devices produce "skid mark" trauma (at least when delivered uncovered upon a balloon) and are associated with a higher risk of end dissection or barotraumas caused at least in part by high balloon pressures and related forces when deforming a balloon-expandable stent for deployment.

Yet, with an appropriate deployment system, self-expanding stents may offer one or more of the following advantages over balloon-expandable models: 1) greater accessibility to distal, tortuous and small vessel anatomy—by virtue of decreasing crossing diameter and increasing compliance relative to a system requiring a deployment balloon, 2) sequentially controlled or "gentle" device deployment, 3) use with low balloon pre-dilatation (if desirable) to reduce barotraumas, 4) strut thickness reduction in some cases reducing the amount of "foreign body" material in a vessel or other body conduit, 5) opportunity to treat neurovasculature—due to smaller crossing diameters and/or gentle delivery options, 6) the ability to easily scale-up a successful treatment system to treat larger vessels or vice versa, 7) a decrease in system complexity, offering potential advantages both in terms of reliability and system cost, 8) reducing intimal hyperplasia, and 9) conforming to tapering anatomy—without imparting complimentary geometry to the stent (though this option exists as well).

At least some of these noted advantages may be realized using a stent 810 as shown in FIG. 8 in connection with the subject deployment system described in further detail below. Naturally, other stent configurations might be used instead. However, the one pictured is well suited for use in small vessels. It may be collapsed to an outer diameter of about 0.018 inch (0.46 mm), or even smaller to about 0.014 inch (0.36 mm)—including the restraint/joint used—and expand to a size (fully unrestrained) between about 1.5 mm (0.059 inch) or 2 mm (0.079 inch) or 3 mm (0.12 inch) and about 3.5 mm (0.14 inch).

In use, the stent will be sized so that it is not fully expanded when fully deployed against the wall of a vessel in order that it will provide a measure of radial force thereto. The force will secure the stent and offer potential benefits in reducing intimal hyperplasia and vessel collapse or even pinning dissected tissue in apposition.

The stent employed in connection with the subject delivery system preferably comprises NiTi that is superelastic at room temperature and above. Also, it is preferably electropolished. The stent may be a drug eluting stent (DES). Such drug can be directly applied to the stent surface(s), or introduced into an appropriate matrix. Note that the term "stent" as used herein refers to any coronary artery stent, other vascular prosthesis, or other radially expanding or expandable prosthesis or scaffold-type implant suitable for the noted treatments or otherwise. Exemplary structures include wire mesh or lattice patterns and coils, though others may be employed in the present invention. A "self expanding" stent is a scaffold-type structure (serving any of a number of purposes) that expands by its own action from a reduced-diameter configuration to an increased-diameter configuration. The "diameter" need not be circular—it may be of any open configuration. Self-expanding materials may be so by virtue of simple elastic behavior, superelastic behavior, a shape memory effect (i.e., heat-activated transformation from martinsite to austenite) or some other manner. Since the stents will remain in the subject's body, the material should be biocompatible or at least be amenable to biocompatible coating. As such, suitable self expanding stent materials for use in the subject invention include NiTi alloy (e.g., NITINOL) and various other alloys or polymers.

For a typical self-expanding stent 0.014 inch delivery system (one in which the maximum nominal outer diameter of the stent/coating and guide member/restraint have a diameter that does not exceed 0.014 inch), the thickness of the NiTi is about 0.0025 inch (0.64 mm) for a stent adapted to expand to 3.5 mm. Such a stent is designed for use in a 3 mm vessel or other body conduit, thereby providing the desired radial force in the manner noted above. Further information regarding radial force parameters in coronary stents may be noted in the article, "Radial Force of Coronary Stents: A Comparative Analysis," Catheterization and Cardiovascular Interventions 46: 380-391 (1999), incorporated by reference herein in its entirety.

As for the stent that may be employed, an optional expanded stent cut pattern 810 is shown in FIG. 8. In one manner of production, the stent is laser (or Electrical Discharge Machining, i.e., EDM) cut from round NiTi tubing, with the flattened-out pattern shown wrapping around the tube as indicated by dashed lines. In such a procedure, the stent is preferably cut in its fully-expanded shape. By initially producing the stent to full size, the approach allows cutting finer details in comparison to simply cutting a smaller tube with slits and then heat-expanding/annealing it into its final (working) diameter. Avoiding post-cutting heat forming also reduces production cost.

Regarding the finer details of the subject stent, necked down bridge or junction sections 812 are provided between adjacent struts 814, wherein the struts define a lattice of closed cells 816. The ends 818 of the cells are preferably rounded-off so as to be atraumatic. To increase stent conformability to tortuous anatomy, the bridge sections can be strategically separated or opened as indicated by broken line. To facilitate such tuning of the stent, the bridge sections are sufficiently long so that fully rounded ends 818 may be formed internally to the lattice just as shown on the outside of the stent if the connection(s) is/are severed to separate adjacent cells 816.

The advantage of the double-concave profile of each strut bridge or junction section 812 is that it reduces material width (relative to what would otherwise be presented by a parallel side profile) to improve trackability and conformability of the stent within the subject anatomy while still maintaining the option for separating/breaking the cells apart.

Further optional features of stent 810 are employed in the cell end regions 818 of the design. Specifically, strut ends 820 increase in width relative to medial strut portions 822. Such a configuration results in a majority of bending (during collapse of the stent) occurring along the length of the struts rather than at the corners of the cells. Longer struts to allow for lower stresses within the stent (and, hence, possibility for higher compression ratios). Shorter struts allow for greater radial force (and concomitant resistance to a radially applied load) upon deployment.

In order to provide a stent that collapses as much as possible (to solid or near-solid structure, such as shown in the fully-loaded systems of the figures) accommodation is made for the stiffer strut ends 820 provided in the design shown in FIG. 8. Namely, the gap 824 between the strut ends 822 is set at a smaller angle as if the stent were already partially collapsed in that area. Thus, the smaller amount of angular deflection that occurs at ends 820 will bring the sections parallel (or nearly so) when the strut medial portions 822 are so-arranged. Radiused sections 826 provide a transition from a medial strut angle α (ranging from about 85 degrees to about 60 degrees) to an end strut angle β (ranging from about 30 to about 0 degrees). In addition, it is noted that gap 824 and angle β may actually be configured to completely close prior to fully collapsing angle α. The value of doing so would be to limit the strains (and hence, stresses) at the strut ends 822 and cell end regions 818 by providing a physical stop to prevent further strain.

By utilizing a design that minimizes strain, very high compression ratios of the stent may be achieved. Compression ratios (from a fully expanded outside diameter to compressed outside diameter—expressed in those terms used by physicians) of as much as 3.5 mm: 0.014 inch (about 10×) are possible—with or without a drug coating and/or restraint used. Compression ratios of 3.0 mm: 0.014 inch (about 8.5×), 3.5 mm: 0.018 inch (about 7.5×), 3.0 mm: 0.018 inch (about 6.5×), 2.5 mm: 0.014 inch (about 7×), 2.5 mm: 0.018 inch (about 5.5×), 2.0 mm: 0.014 inch (about 5.5×), 2.0 mm: 0.018 inch (about 4.5×) offer utility not heretofore possible with existing systems as well.

These selected sizings (and expansion ratios) correspond to treating 1.5 to 3.0 mm vessels by way of delivery systems adapted to pass through existing balloon catheter and microcatheter guidewire lumen. In other words, the 0.014 inch and 0.018 inch systems are designed to corresponding common guidewire sizes. The system may also be scaled to other common guidewire sizes (e.g., 0.22 inch/0.56 mm or 0.025 inch/0.64 mm) while offering advantages over known systems.

While designing the delivery systems to have a crossing profile corresponding to common guidewire sizes, especially for full-custom systems, intermediate sizes may be employed. Still further, it is contemplated that the system sizing may be set to correspond to French (FR) sizing. In that case, system sizes contemplated range at least from 1 to 1.5 FR, whereas the smallest know balloon-expandable stent delivery systems are in the size range of about 3 to about 4 FR.

At least when produced at the smallest sizes (whether in a even/standard guidewire or FR size, or otherwise), the system enables a substantially new mode of stent deployment in which delivery is achieved through an angioplasty balloon catheter or small microcatheter lumen. Further discussion and details of "through the lumen" delivery is presented in the above-referenced "Balloon Catheter Lumen Based Stent Delivery Systems" patent application.

In "small vessel" cases or applications (where the vessel to be treated has a diameter up to about 3.0 mm), it may also be advantageous to employ a stent delivery system sized at between about 0.022 to about 0.025 inch in diameter. Such a system can be used with catheters compatible with 0.022 inch diameter guidewires.

While such a system may not be suitable for reaching the very smallest vessels, in reaching the larger of the small vessels (i.e., those having a diameter of about 2.5 mm or larger), even this variation of the invention is quite advantageous in comparison to known systems. By way of comparison, the smallest known over-the-guidewire delivery system (the "Pixel" system—produced by Guidant) that is adapted to treat vessels between 2 and 2.5 mm has a crossing profile of 0.036 inch (0.91 mm). A system described in U.S. Patent Publication No. 2002/0147491 for treating small vessels is purported to be capable of being made as small as 0.026 inch (0.66 mm) in diameter.

With respect to the Pixel and '491 systems, however, it must be appreciated that a further decrease in stent size may be practically impossible in view of materials limitations and functional parameters of the stent. Instead, the present invention offers a different paradigm for delivery devices and stents that are scalable to the sizes noted herein.

By virtue of the approaches taught herein, it is feasible to design system diameters to match (or at least nearly match) common guidewire size diameters (i.e., 0.014, 0.018 and 0.022 inch) for small vessel delivery applications. As noted above, doing so facilitates use with compatible catheters and opens the possibility for methodology employing the same as elaborated upon below and in the above-referenced "Balloon Catheter Lumen Based Stent Delivery Systems" patent application.

Of further note, it may be desired to design a variation of the subject system for use in deploying stents in larger, peripheral vessels, bilary ducts or other hollow body organs. Such applications involve a stent being emplaced in a region having a diameter from about 3.5 to about 13 mm (0.5 inch). In this regard, the scalability of the present system, again, allows for creating a system adapted for such use that is designed around a common wire size. Namely, a 0.035 to 0.039 inch (3 FR) diameter crossing profile system is advantageously provided in which the stent expands (unconstrained) to a size between about roughly 0.5 mm and about 1.0 mm greater than the vessel or hollow body organ to be treated. Sufficient stent expansion is easily achieved with the exemplary stent pattern shown in FIG. 8.

Again, as a matter of comparison, the smallest delivery systems known to applicants for stent delivery in treating such larger-diameter vessels or biliary ducts is a 6 FR system (nominal 0.084 inch outer diameter), which is suited for use in an 8 FR guiding catheter. Thus, even in the larger sizes, the present invention affords opportunities not heretofore possible in achieving delivery systems in the size range of a commonly used guidewire, with the concomitant advantages discussed herein.

Several known stent delivery systems are compatible with (i.e., may be delivered over) common-sized guides wires ranging from 0.014 inch to 0.035 inch (0.89 mm). Yet, none of the delivery systems are themselves known to be so-sized.

As for the manner of using the inventive system as optionally configured, FIGS. 3A-3L illustrate an exemplary angioplasty procedure. Still, the delivery systems and stents or implants described herein may be used otherwise—especially as specifically referenced herein.

Figure 9B:
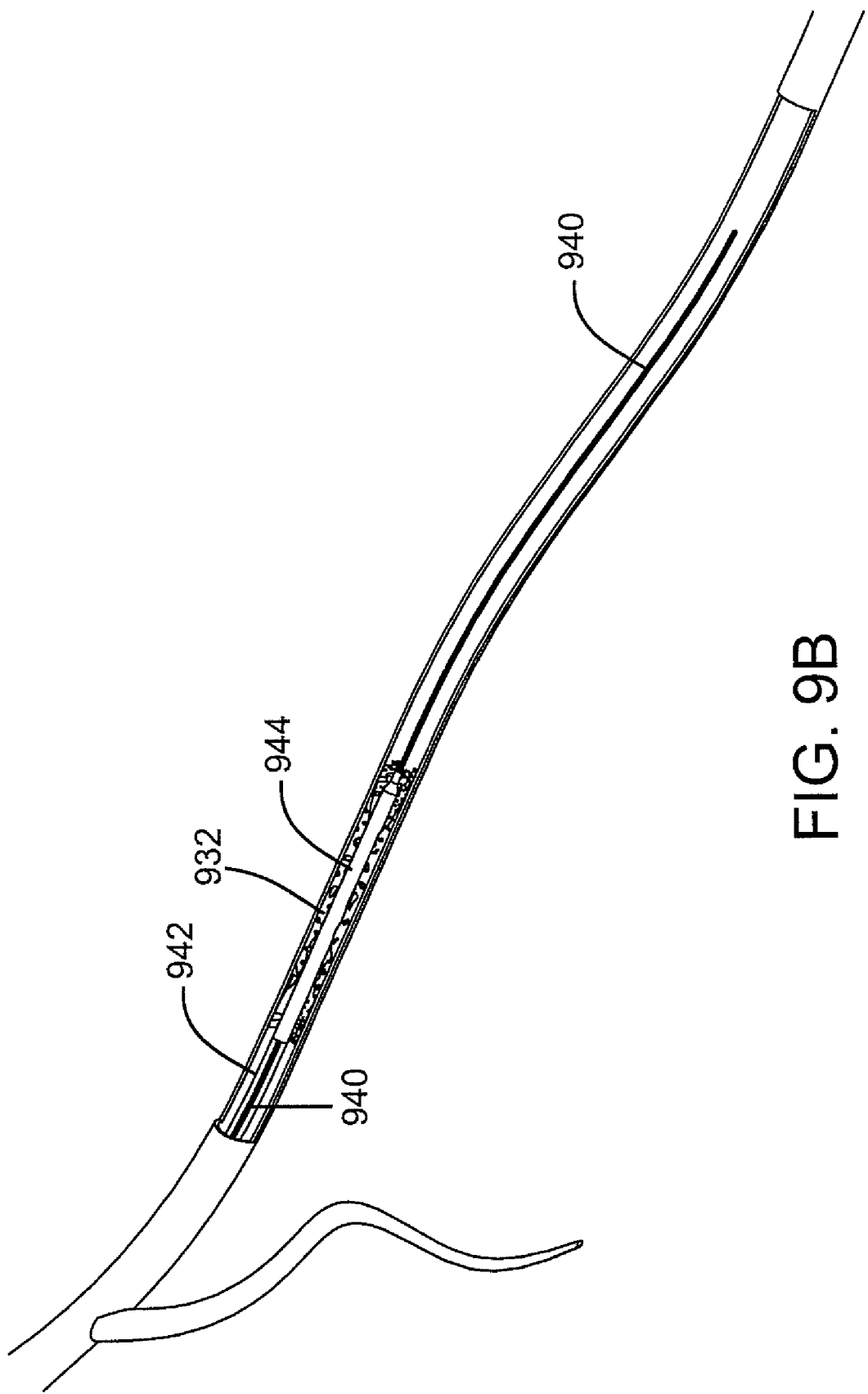

Turning to FIG. 9A, a coronary artery 930 is shown partially or totally occluded by plaque at a treatment site/lesion 932. Into this vessel, a guidewire 40 is passed distal to the treatment site. In FIG. 9B, a balloon catheter 942 with a balloon tip 944 is passed over the guidewire, aligning the balloon portion with the lesion (the balloon catheter shaft proximal to the balloon is shown in cross section with guidewire 940 therein).

Figure 9C:
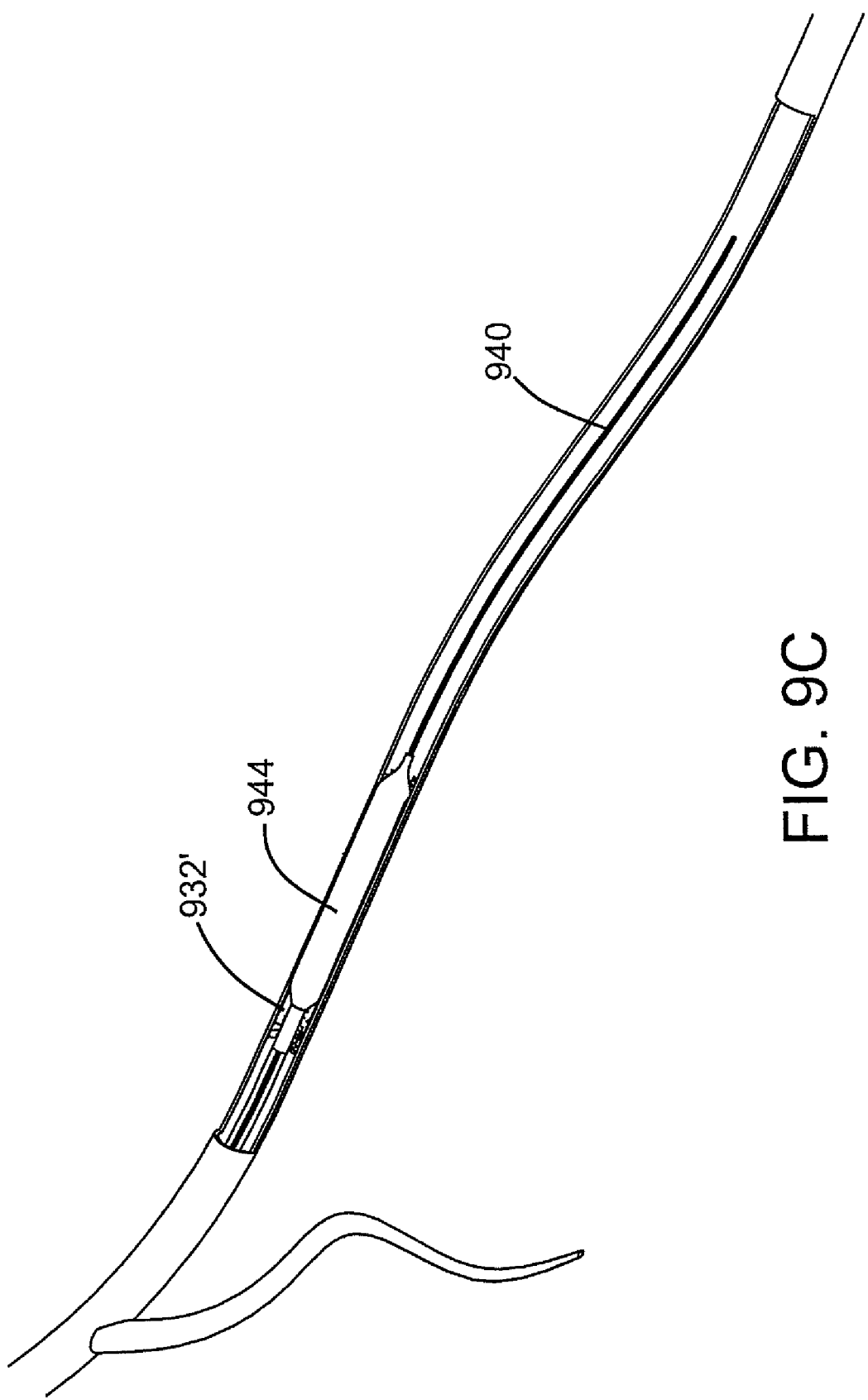

As illustrated in FIG. 9C, balloon 944 is expanded (dilatated or dialated) in performing an angioplasty procedure, opening the vessel in the region of lesion 932. The balloon expansion may be regarded as "predilatation" in the sense that it will be followed by stent placement (and optionally) a "postdilataton" balloon expansion procedure.

Next, the balloon is at least partially deflated and passed forward, beyond the dilate segment 932' as shown in FIG. 9D.

Figure 9E:
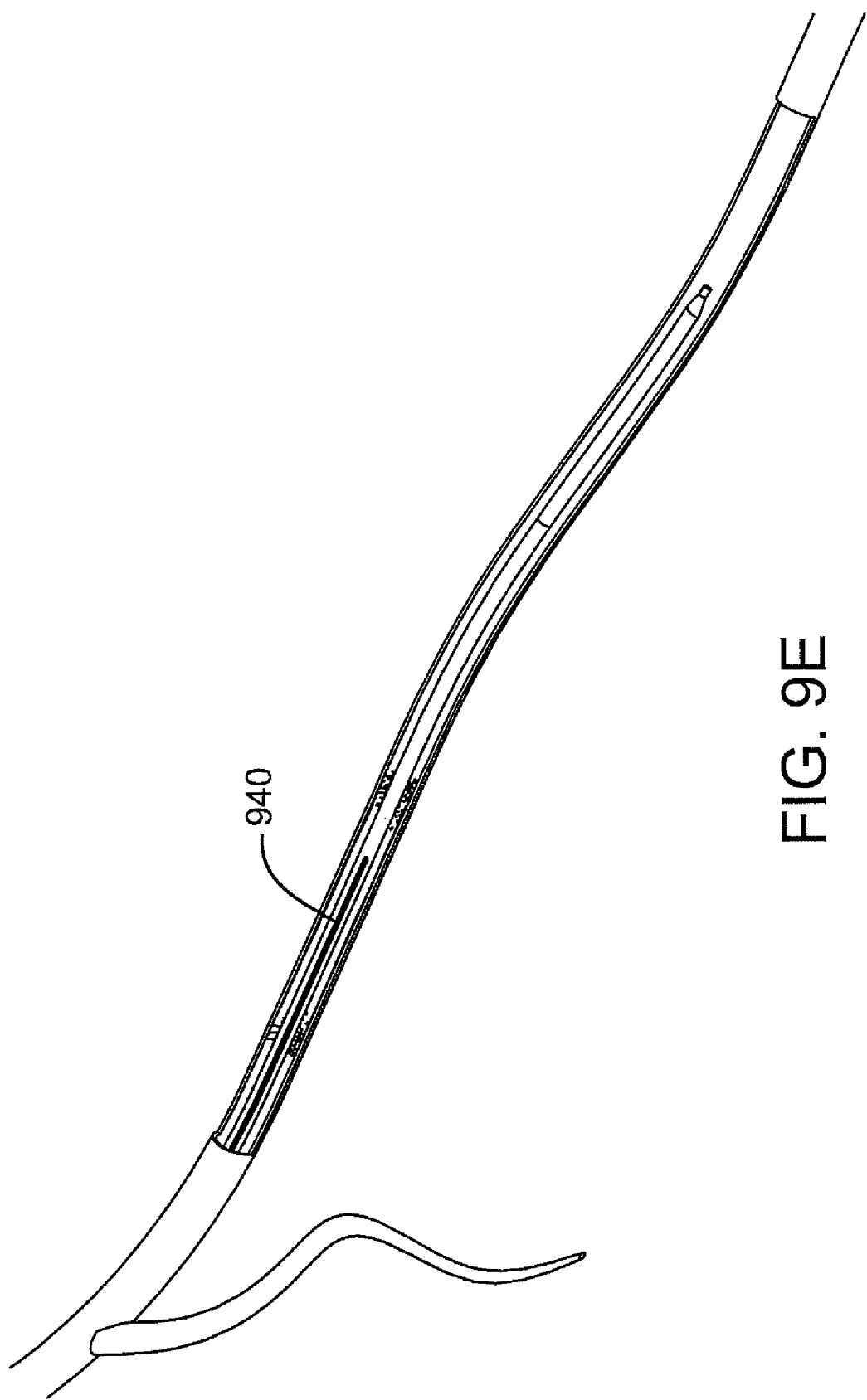
Figure 9F:
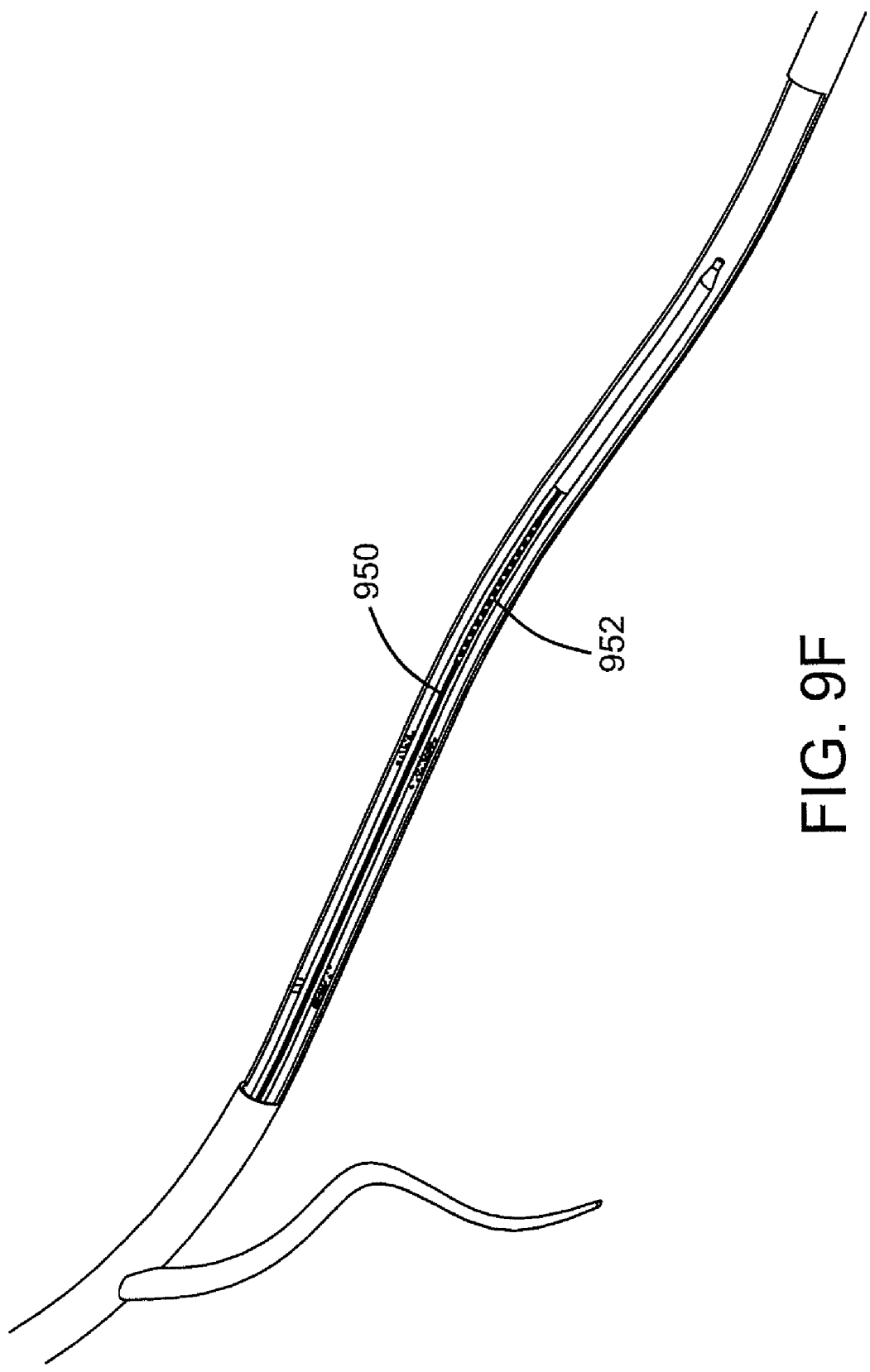

At this point, guidewire 940 is removed as illustrated in FIG. 9E. It is exchanged for a delivery guide member 950 carrying stent 952 as further described below. This exchange is illustrated in FIGS. 3E and 3F.

However, it should be appreciated that such an exchange need not occur. Rather, the original guidewire device inside the balloon catheter (or any other catheter used) may be that of item 950, instead of the standard guidewire 940 shown in FIG. 9A. Thus, the steps depicted in FIGS. 9E and 9F (hence, the figures also) may be omitted. In addition, there maybe no use in performing the step in FIG. 9D of advancing the balloon catheter past the lesion, since such placement is merely for the purpose of avoiding disturbing the site of the lesion by moving a guidewire past the same.

Figure 9G:
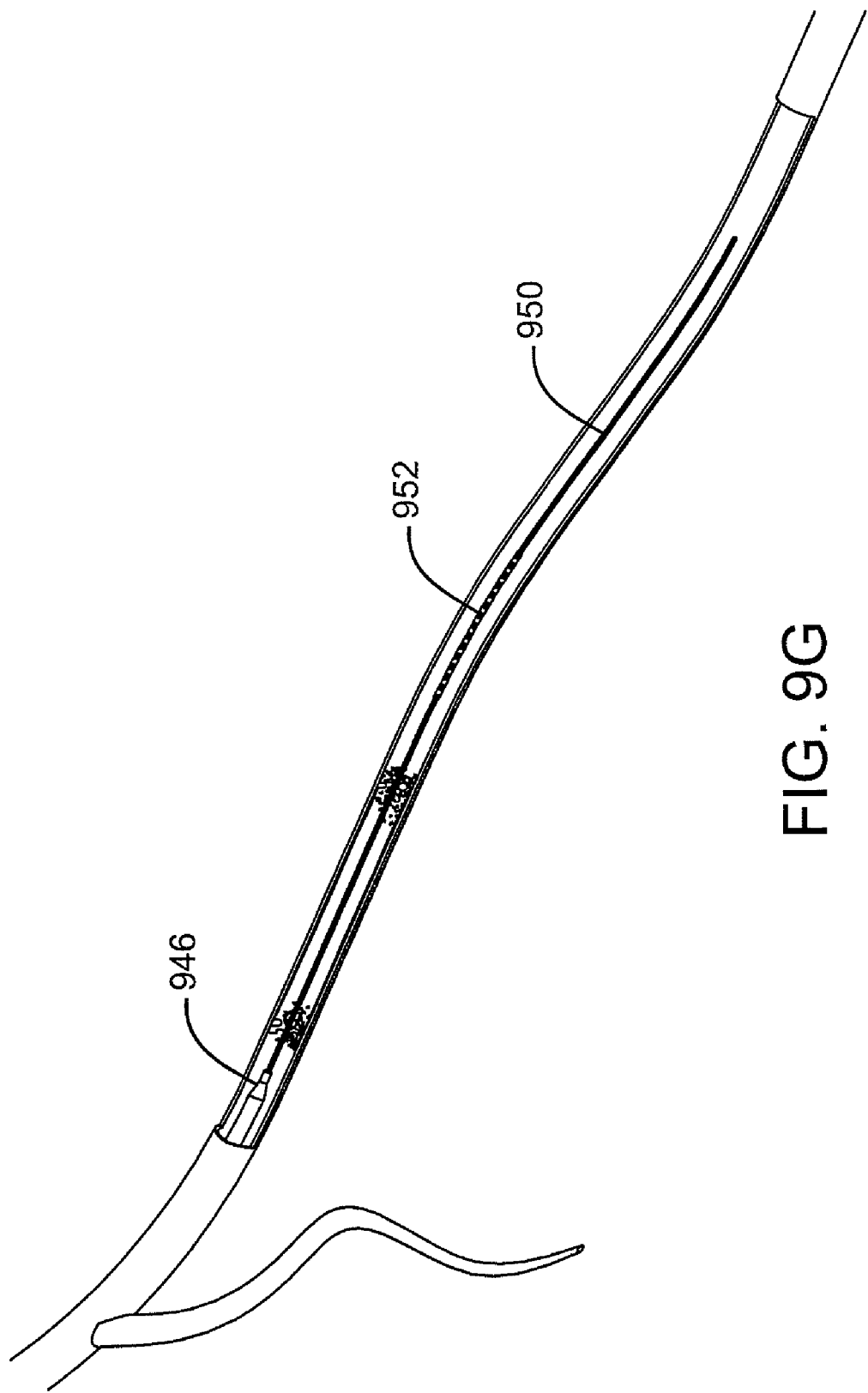
Figure 9H:
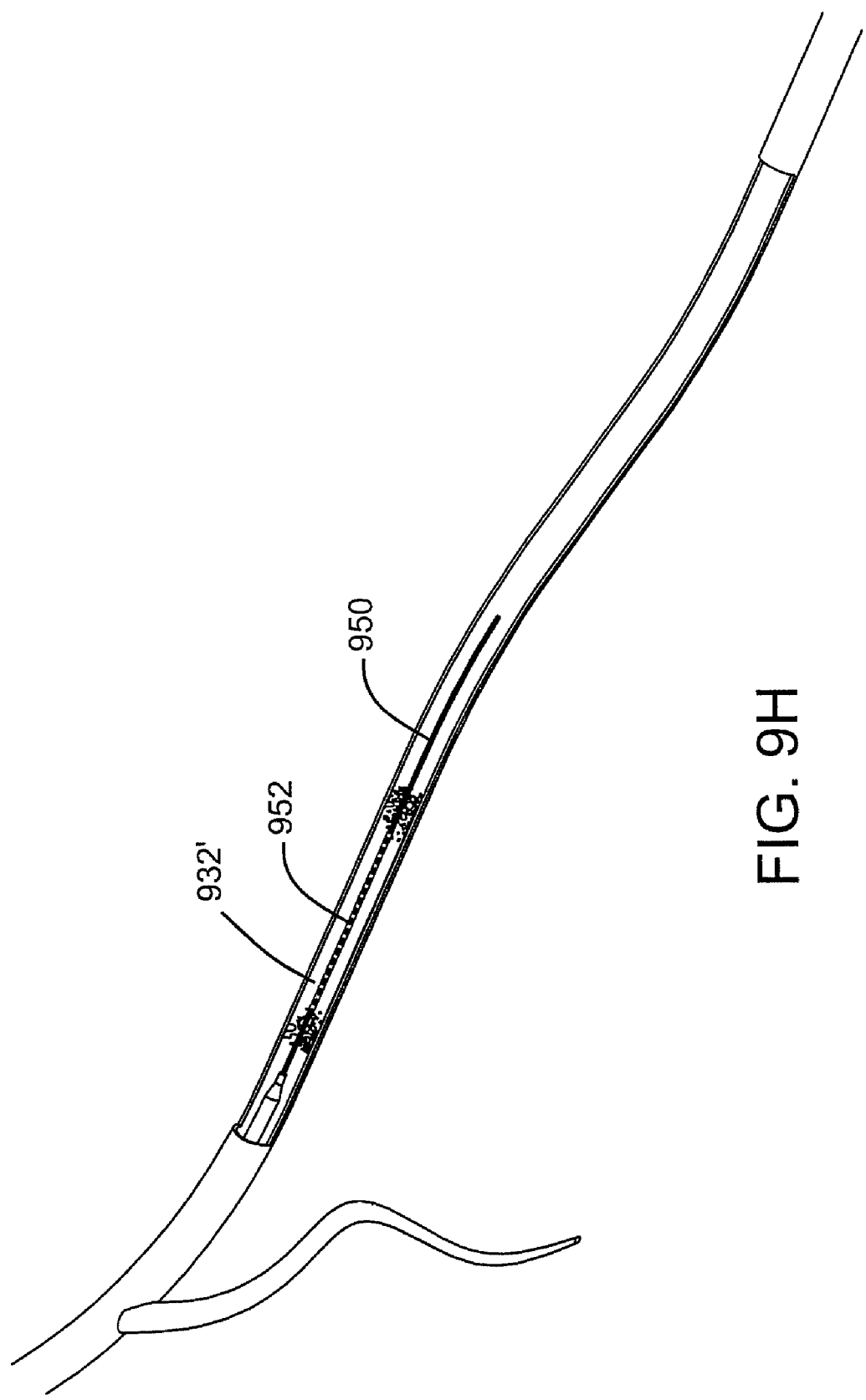
Figure 91:
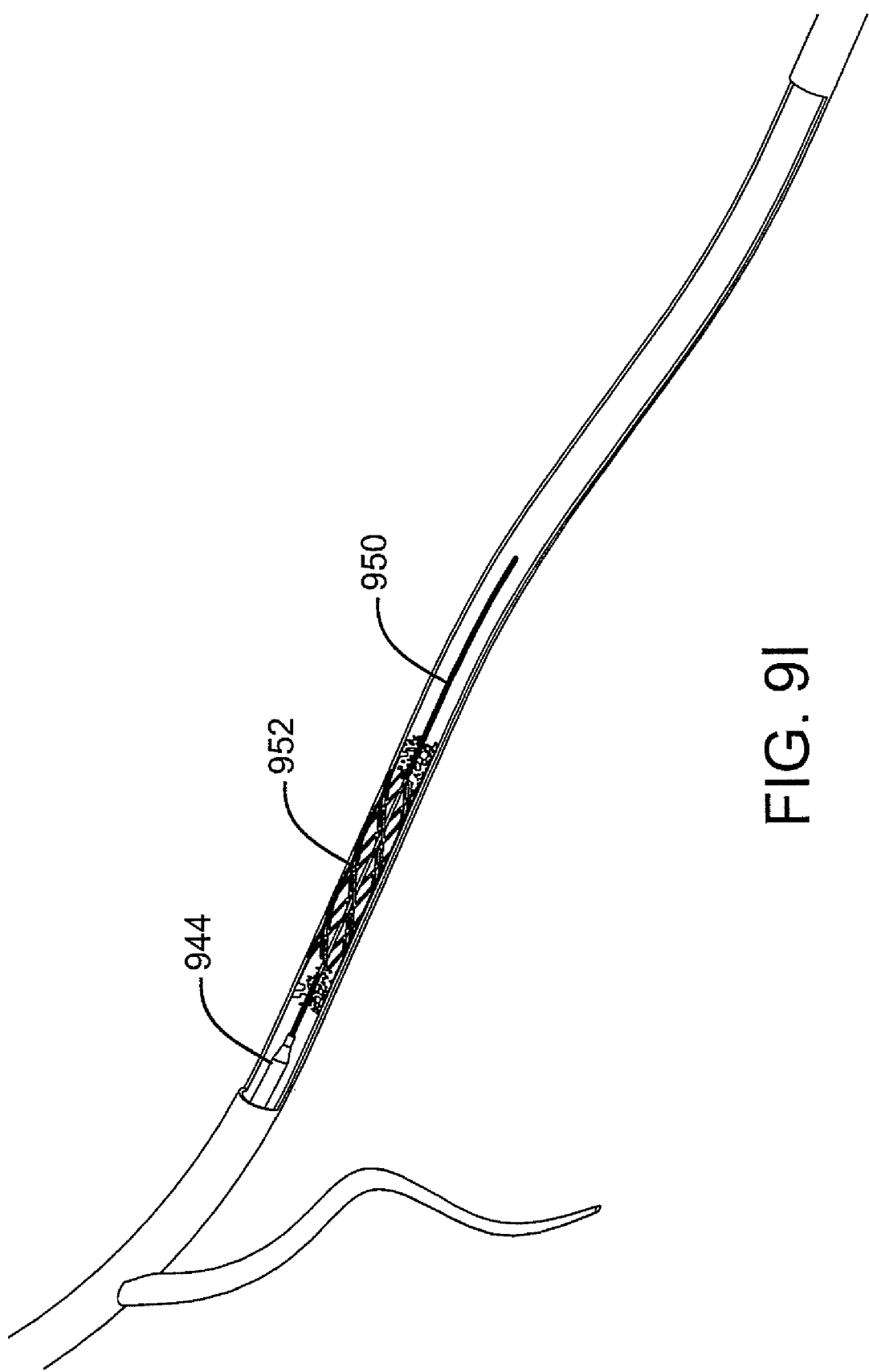

FIG. 9G illustrates the next act in either case. Particularly, the balloon catheter is withdrawn so that its distal end 946 clears the lesion. Preferably, delivery guide 950 is held stationary, in a stable position. After the balloon is pulled back, so is delivery device 950, positioning stent 952 where desired. Note, however, that simultaneous retraction may be undertaken, combining the acts depicted in FIGS. 3G and 3H. Whatever the case, it should also be appreciated that the coordinated movement will typically be achieved by virtue of skilled manipulation by a doctor viewing one or more radiopaque features associated with the stent or delivery system under medical imaging.

Figure 9J:
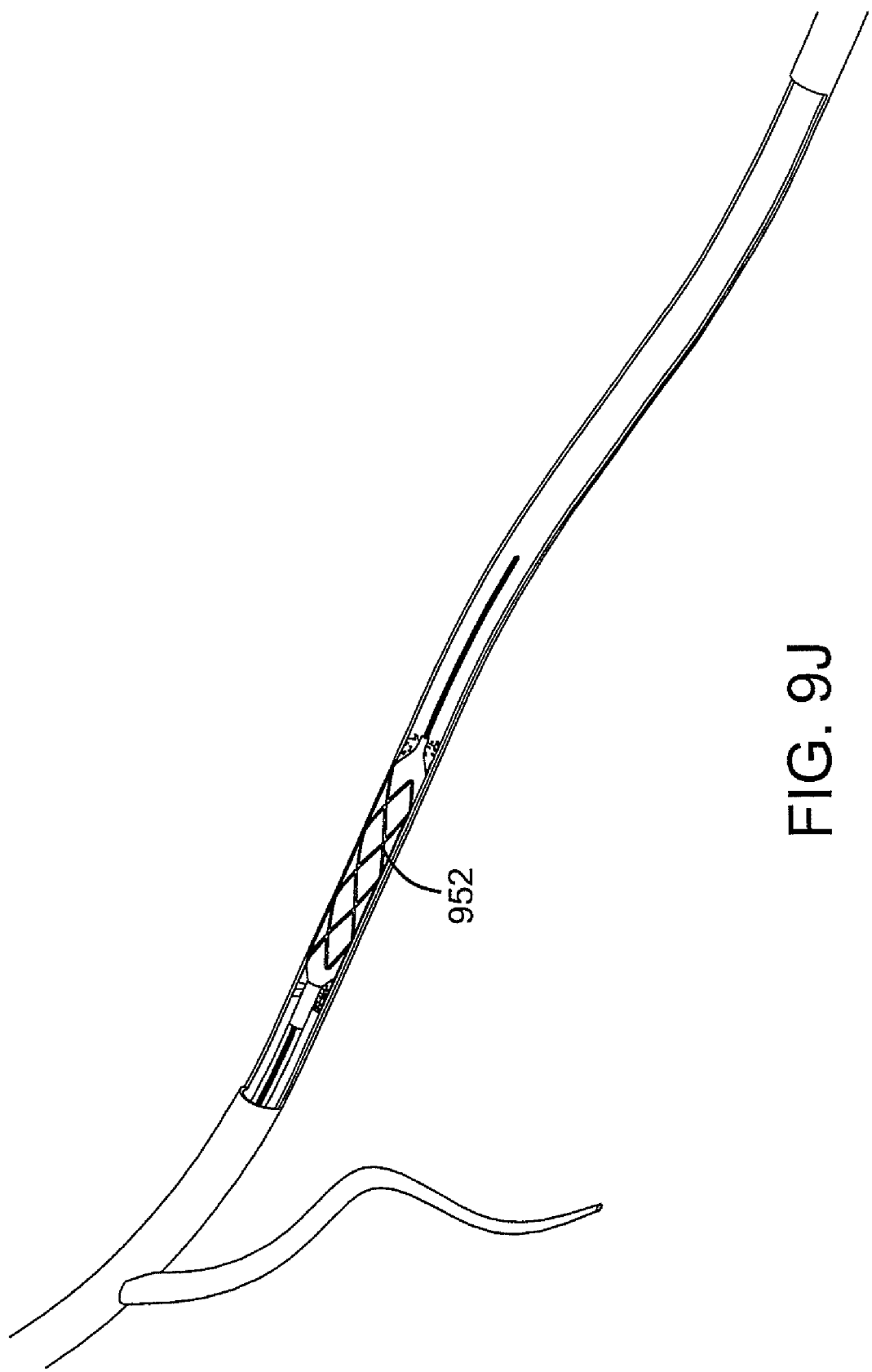

Once placement of the stent across from dilated segment 932' is accomplished, stent deployment commences. The manner of deployment is elaborated upon below. Upon deployment, stent 952 assumes an at least partially expanded shape in apposition to the compressed plaque as shown in FIG. 9I. Next, the aforementioned postdilatation may be effected as shown in FIG. 9J by positioning balloon 944 within stent 952 and expanding both. This procedure may further expand the stent, pushing it into adjacent plaque—helping to secure each.

Naturally, the balloon need not be reintroduced for postdilatation, but it may be preferred. Regardless, once the delivery device 950 and balloon catheter 942 are withdrawn as in FIG. 9K, the angioplasty and stenting procedure at the lesion in vessel 930 is complete. FIG. 9L shows a detailed view of the emplaced stent and the desired resultant product in the form of a supported, open vessel.

In the above description, a 300 cm extendable delivery system is envisioned. Alternatively, the system can be 190 cm to accommodate a rapid exchange of monorail type of balloon catheter as is commonly known in the art. Of course, other approaches may be employed as well.

Furthermore, other endpoints may be desired such as implanting an anchoring stent in a hollow tubular body organ, closing off an aneurysm, delivering a plurality of stents, etc. In performing any of a variety of these or other procedures, suitable modification will be made in the subject methodology. For example, in treating neurovasculature, peripheral vessel procedures or others there may be no need for a balloon catheter. Instead, a standard catheter or microcatheter may be employed to access a target site. Still, a balloon catheter might later be used to effect postdilitation of the prosthesis. As another alternative, a balloon catheter might be employed for predilatation (even post dilitation) and a regular catheter or microcatheter employed in connection with site access and stent delivery.

The procedure shown is depicted merely because it illustrates a potentially preferred mode of practicing the subject invention, despite the invention's potential for broader applicability in the various fields or applications noted herein as well as others. In addition, variation of the illustrated procedure itself is contemplated—both in connection with those possible modifications noted above or others as may be apparent to those with skill in the art.

Applications

The implant delivery system may be used in mammalian subjects, preferably humans. Mammals include, but are not limited to, primates, farm animals, sport animals, cats, dogs, rabbits, mice, and rats.

The system may be employed for implant delivery into lumens of tubular organs including, but not limited to, blood vessels (including intracranial vessels, large vessels, peripheral vessels, aneurysms, arteriovenous malformations, arteriovenous fistulas), ureters, bile ducts, fallopian tubes, cardiac chambers, ducts such as bile ducts and mammary ducts, large and small airways, and hollow organs, e.g., stomach, intestines, and bladder. The system may also be employed for implant delivery into solid organs or tissues including, but not limited to, skin, muscle, fat, brain, liver, kidneys, spleen, and benign and malignant tumors. Preferably, the implant is delivered to a target site in a blood vessel lumen. Of special interest are coronary and neurovascular application. However, the invention is neither limited to such applications or those specifically noted herein.

Clinically, the system may generally be used to treat stenosis of various tubular organs, arising from such etiologies as atherosclerosis, autoimmune conditions, scarring, or exterior compression, e.g., as may be seen with a neoplastic process. The system may also be used to treat medical conditions in which luminal occlusion is desired, e.g., to treat aneurysms, arteriovenous fistulas, and arteriovenous malformations. Furthermore, the system may be employed to deliver implants into such areas as joint spaces, spinal discs, and the intraperitoneal or extraperitoneal spaces.

General Features

In regard to any such system, it is to be understood that conventional materials and techniques may be employed in the system construction. In this regard, it will often be desired to provide a lubricious coating or cover between moving components to reduce internal system friction.

In addition, it is to be understood that various radiopaque markers or features may be employed in the system to 1) locate stent position and length, 2) indicated device actuation and stent delivery and/or 3) locate the distal end of the delivery guide. As such, various platinum (or other radiopaque material) bands or other markers (such as tantalum plugs) may be variously incorporated into the system. Alternatively, or additionally, the stent stop or blocker member may be made of radiopaque material. Especially where the stent employed may shorten somewhat upon deployment, it may also be desired to align radiopaque features with the expected location (relative to the body of the guide member) of the stent upon deployment. For example, it may be desired to incorporate radiopaque features into the restraint and/or bridge or connector sections so that the deployment motion of the device is visible under fluoroscopy. Exemplary markers that may be of use are shown at a proximal end of the stent in FIG. 10 as elements A and A'—on the delivery guide body and restraint, respectively—and at a distal end of the stent on the sheath as element B, or otherwise.

Connections are made between parts in any of a number of manners including fusing, bonding, welding (by resistance, laser, chemically, ultrasonically, etc), gluing, pinning, crimping, clamping or otherwise mechanically or physically joining, attaching or holding components together (permanently or temporarily). Except where particularly noted, materials conventionally employed in the medical arts may be employed.

All existing subject matter mentioned herein (e.g., publications, patents, and patent applications, etc.) cited herein are hereby incorporated by reference in its/their entirety for all purposes to the same extent as if each individual publication, patent, or patent application were specifically and individually indicated to be so incorporated by reference. The referenced items are provided solely for their disclosure prior to the filing date of the present application. Nothing herein is to be construed as an admission that the present invention is not entitled to antedate such material by virtue of prior invention.

Furthermore, it is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process act(s) or step(s), to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

Reference to a singular item, includes the possibility that there are plural of the same items present. More specifically, as used herein and in the appended claims, the singular forms "a," "and," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs.

CLAIMS

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit and scope of the appended claims. The breadth of the present invention is to be limited only by the literal or equitable scope of the following claims. That being said,

We claim:

1. A method of treating a vessel in a human body comprising:

passing a balloon catheter, which has a balloon, over an elongate stent carrying member, which has a stent attached thereto and serves as a guidewire for the balloon catheter, to a treatment site in a vessel in a human body such that said balloon is aligned with said treatment site; and expanding said balloon while said balloon catheter is over said elongate stent carrying member with said balloon aligned with the treatment site to dilate the treatment site prior to deployment of said stent.

2. The method of claim 1 wherein said balloon is at least partially deflated and said balloon catheter is moved to allow deployment of said stent from said elongate stent carrying member at the treatment site.

3. The method of claim 2 wherein said balloon is at least partially deflated and said balloon catheter is moved to allow deployment of said stent from said elongate stent carrying member at the treatment site without removing said balloon catheter from said elongate stent carrying member.

4. The method of claim 1 wherein said balloon catheter has a distal end and said balloon catheter is moved so that said distal end clears the treatment site.

5. The method of any one of claims 2, 3, and 4 wherein said stent is deployed at the treatment site and assumes an at least partially expanded shape and said balloon positioned in the deployed stent and expanded to expand said stent without removing said balloon catheter from said elongate stent carrying member.

6. The method of claim 1 wherein said stent is a self-expanding stent.

7. An angioplasty method comprising:
positioning an elongate stent carrying member with a self-expanding stent directly attached thereto at a location in a vessel, which has a lesion;
passing a balloon catheter, which has a balloon, over said elongate stent carrying member prior to deploying said stent from said elongate stent carrying member wherein said elongate stent carrying member serves as a guidewire for said balloon catheter;
aligning said balloon of said balloon catheter with the lesion; and
expanding said balloon in performing the angioplasty.

8. The method of claim 7 wherein said balloon is expanded at the lesion in performing the angioplasty without removing said balloon catheter from said elongate stent carrying member.

9. The method of claim 8 wherein after said balloon is expanded, it is at least partially deflated and moved away from the lesion after which said stent is deployed from said elongate stent carrying member at the lesion where said stent assumes an at least partially expanded shape.

10. The method of claim 9 wherein said balloon catheter is repositioned so that said balloon is in the deployed stent after which said balloon is expanded to further expand the stent.

11. A method for treating a lesion in a human body comprising:
positioning an elongate stent carrying member, which has a self-expanding stent attached thereto, at a location in a vessel with the stent near a lesion;
passing a balloon catheter with an expandable balloon over said elongate stent carrying member, which serves as a guidewire for said balloon catheter, to the lesion prior to deploying said stent from said elongate stent carrying member and dilating the lesion with said balloon, which surrounds the elongate stent carrying member;
moving said balloon catheter after at least partial deflation thereof to allow deployment of said self-expanding stent at the lesion, while maintaining said balloon catheter on said elongate stent carrying member; and
deploying said self-expanding stent from said elongate stent carrying member at the dilated lesion wherein the stent assumes an at least partially expanded shape.

12. The method of claim 11 further comprising moving said balloon catheter over said elongate stent carrying member after deployment of said stent and positioning said balloon catheter balloon in the deployed stent and expanding the balloon catheter balloon and deployed stent.

13. A method of treating a vessel in a human body comprising:
passing a balloon catheter, which has a balloon, over an elongate stent carrying member, which has a stent attached thereto and serves as a guidewire for the balloon catheter as the balloon is passed thereover, while advancing said balloon catheter toward a treatment site in a vessel in a human body prior to deploying the stent from said elongate stent carrying member;
aligning said balloon with said treatment site prior to deploying the stent from said elongate stent carrying member; and
subsequent to said aligning said balloon with said treatment site, expanding said balloon while said balloon catheter is over said elongate stent carrying member with said stent attached thereto and said balloon aligned with the treatment site to dilate the treatment site prior to deployment of said stent.

14. The method of any one of claims 1, 7, 11 and 13, wherein at least one releasable joint maintains at least a section of the stent at a delivery diameter until release of the at least one releasable joint and the stent is releasably attached to the elongate stent carrying member by the at least one releasable joint.

15. The method of claim 14 wherein the at least one releasable joint is configured to release upon application of a suitable DC current.

16. The method of claim 14 wherein the at least one releasable joint is mechanically released to release the stent.

17. The method of claim 14 wherein the at least one releasable joint is configured to release upon application of fluid pressure in the stent carrying member where a fluid director is slidably located to direct fluid to and release the at least one releasable joint.

18. The method of claim 14 wherein an actuator in the stent carrying member is used to release the at least one releasable joint.

* * * * *